United States Patent
Johs et al.

(10) Patent No.: US 7,193,710 B1
(45) Date of Patent: Mar. 20, 2007

(54) ROTATING OR ROTATABLE COMPENSATOR SPECTROSCOPIC ELLIPSOMETER SYSTEM INCLUDING MULTIPLE ELEMENT LENSES

(75) Inventors: Blaine D. Johs, Lincoln, NE (US); Martin M. Liphardt, Lincoln, NE (US); Jeffrey S. Hale, Lincoln, NE (US); Craig M. Herzinger, Lincoln, NE (US); Steven E. Green, Lincoln, NE (US); Ping He, Lincoln, NE (US); John A. Woollam, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 239 days.

(21) Appl. No.: 10/829,620

(22) Filed: Apr. 22, 2004

Related U.S. Application Data

(63) Continuation-in-part of application No. 10/034,800, filed on Dec. 28, 2001, now Pat. No. 6,822,738, and a continuation-in-part of application No. 09/583,229, filed on May 30, 2000, now Pat. No. 6,804,004, and a continuation-in-part of application No. 09/162,217, filed on Sep. 29, 1998, now Pat. No. 6,034,777, and a continuation-in-part of application No. 09/033,694, filed on Mar. 3, 1998, now Pat. No. 5,963,327, and a continuation-in-part of application No. 09/144,764, filed on Aug. 31, 1998, now Pat. No. 5,969,818, and a continuation-in-part of application No. 09/419,794, filed on Oct. 18, 1999, and a continuation-in-part of application No. 09/144,764, filed on Aug. 31, 1998, application No. 10/829,620, which is a continuation-in-part of application No. 10/699,540, filed on Nov. 1, 2003, and a continuation-in-part of application No. 09/945,962, filed on Sep. 4, 2001, and a continuation-in-part of application No. 09/517,125, filed on Feb. 29, 2000, and a continuation-in-part of application No. 09/246,888, filed on Feb. 8, 1999, now Pat. No. 6,084,675, which is a continuation-in-part of application No. 08/912,211, filed on Aug. 15, 1997, now Pat. No. 5,872,630, which is a continuation-in-part of application No. 08/530,892, filed on Sep. 20, 1995, now Pat. No. 5,666,201, and a continuation-in-part of application No. 08/618,820, filed on Mar. 20, 1996, now Pat. No. 5,706,212, application No. 10/829,620, which is a continuation-in-part of application No. 09/225,118, filed on Jan. 4, 1999, now Pat. No. 6,084,674, and a continuation-in-part of application No. 09/223,822, filed on Jan. 4, 1999, now Pat. No. 6,118,537, and a continuation-in-part of application No. 09/232,257, filed on Jan. 19, 1999, now Pat. No. 6,141,102, and a continuation-in-part of application No. 09/225,371, filed on Jan. 4, 1999, now Pat. No. 6,100,981, and a continuation-in-part of application No. 09/225,076, filed on Jan. 4, 1999, now Pat. No. 5,963,325, which is a continuation-in-part of application No. 08/997,311, filed on Dec. 23, 1997, now Pat. No. 5,946,098.

(60) Provisional application No. 60/527,638, filed on Dec. 8, 2003, provisional application No. 60/527,554, filed on Dec. 6, 2003, provisional application No. 60/094,104, filed on Jul. 24, 1998.

(51) Int. Cl.
*G01J 4/00* (2006.01)
(52) U.S. Cl. ...................................... 356/369
(58) Field of Classification Search ............... 356/369, 356/153, 399–402
See application file for complete search history.

(56) References Cited

U.S. PATENT DOCUMENTS

| | | |
|---|---|---|
| 2,700,918 A | 2/1955 | Osterberg et al. |
| 3,183,763 A | 5/1965 | Moester |
| 3,992,104 A | 11/1976 | Watanabe ................. 356/117 |
| 4,053,232 A | 10/1977 | Dill et al. ................. 356/118 |
| 4,105,338 A | 8/1978 | Kuroha ..................... 356/118 |
| 4,210,401 A | 7/1980 | Batten ...................... 356/369 |
| 4,332,476 A | 6/1982 | Stenberg et al. ........... 356/369 |
| 4,355,903 A | 10/1982 | Sandercock ............... 356/382 |

| | | | |
|---|---|---|---|
| 4,373,817 A | 2/1983 | Coates | 356/384 |
| 4,556,292 A | 12/1985 | Mathyssek et al. | 350/394 |
| 4,636,075 A | 1/1987 | Knollenberg | 356/336 |
| 4,647,207 A | 3/1987 | Bjork et al. | 356/369 |
| 4,668,860 A | 5/1987 | Anthon | 250/225 |
| 4,750,822 A | 6/1988 | Rosencwaig et al. | 356/445 |
| 4,826,321 A | 5/1989 | Coates et al. | 356/351 |
| 4,838,695 A | 6/1989 | Mansuripur et al. | 356/369 |
| 4,893,932 A | 1/1990 | Knollenberg | 356/369 |
| 5,042,951 A | 8/1991 | Gold et al. | 356/369 |
| 5,045,704 A | 9/1991 | Coates | 356/448 |
| 5,324,953 A * | 6/1994 | Yoshitake et al. | 250/557 |
| 5,329,357 A | 7/1994 | Bernoux et al. | 356/369 |
| 5,333,052 A | 7/1994 | Finarov | 356/369 |
| RE34,783 E | 11/1994 | Coates | 250/372 |
| 5,373,359 A | 12/1994 | Woollam et al. | 356/328 |
| 5,475,525 A | 12/1995 | Tournois et al. | 359/245 |
| 5,504,582 A | 4/1996 | Johs et al. | 356/369 |
| 5,521,706 A | 5/1996 | Green et al. | 356/369 |
| 5,581,350 A | 12/1996 | Chen et al. | 356/369 |
| 5,596,411 A | 1/1997 | Fanton et al. | |
| 5,608,526 A | 3/1997 | Piwonka-Corle et al. | 356/369 |
| 5,666,201 A | 9/1997 | Johs et al. | 356/369 |
| 5,706,212 A | 1/1998 | Thompson et al. | 364/525 |
| 5,757,494 A | 5/1998 | Green et al. | 356/369 |
| 5,764,365 A * | 6/1998 | Finarov | 356/630 |
| 5,793,480 A | 8/1998 | Lacey et al. | 356/73 |
| 5,798,837 A | 8/1998 | Aspnes et al. | 356/369 |
| 5,872,630 A * | 2/1999 | Johs et al. | 356/369 |
| 5,877,859 A | 3/1999 | Aspnes et al. | 356/369 |
| 5,917,594 A | 6/1999 | Norton | 356/327 |
| 5,946,098 A | 8/1999 | Johs et al. | 356/364 |
| 5,956,145 A | 9/1999 | Green et al. | 356/364 |
| 5,956,147 A * | 9/1999 | Jellison et al. | 356/369 |
| 5,963,325 A | 10/1999 | Johs et al. | 356/364 |
| 5,963,327 A | 10/1999 | He et al. | 356/369 |
| 5,973,787 A * | 10/1999 | Aspnes et al. | 356/369 |
| 6,084,674 A | 7/2000 | Johs et al. | 356/364 |
| 6,084,675 A | 7/2000 | Herzinger et al. | 356/369 |
| 6,100,981 A | 8/2000 | Johs et al. | 356/364 |
| 6,118,537 A | 9/2000 | Johs et al. | 356/369 |
| 6,141,102 A | 10/2000 | Johs et al. | 356/364 |
| 6,181,421 B1 * | 1/2001 | Aspnes et al. | 356/369 |
| 6,268,917 B1 | 7/2001 | Johs | 356/369 |
| 2005/0041250 A1 * | 2/2005 | Opsal | 356/369 |

OTHER PUBLICATIONS

Paper by Johs, titled "Regression Calibration Method for Rotating Element Ellipsometers", Thin Solid Films, 234 (1993).

Paper, by Gottesfeld et al., titled "Combined Ellipsometer and Reflectometer Measurements of Surface Processes on Nobel Metals Electrodes", Surface Sci., 56 (1976).

Paper by Smith, titled "An Automated Scanning Ellipsometer", Surface Science, vol. 56, No. 1. (1976).

Papers, by Azzam and Azzam et al. are also identified as concerning alternative approaches to the goal of the present invention, and are titled: "Multichannel Polarization State Detectors For Time-Resolved Ellipsometry", Thin Solid Film, 234 (1993).

"Spectrophotopolarimeter Based On Multiple Reflections In A Coated Dielectric Slab", Thin Solid Films 313 (1998).

"General Analysis And Optimization Of The Four-Detector Photopolarimeter", J. Opt. Soc. Am., A, vol. 5, No. 5 (May 1988).

"Accurate Calibration Of Four-Dectector Photopolarimeter With Imperfect Polarization Optical Elements", J. Opt. Soc. Am., vol. 6, No. 10, (Oct. 1989).

Review paper by Collins, titled "Automatic Rotating Element Ellipsometers: Calibration, Operation and Real-Time Applications", Rev. Sci. Instrum., 61(8) (1990), is identified for general information.

* cited by examiner

*Primary Examiner*—Gregory J. Toatley, Jr.
*Assistant Examiner*—Isiaka O. Akanbi
(74) *Attorney, Agent, or Firm*—James D. Welch

(57) ABSTRACT

Disclosed are spectroscopic ellipsometer systems which include polarizer and analyzer elements which remain fixed in position during data acquisition, and at least one continuously rotating or step-wise rotatable compensator which transmits an electromagnetic beam therethrough and imposes a continuously variable or plurality of sequentially discrete polarization states on a beam of electromagnetic radiation; and at least one multiple element lens which also transmits the electromagnetic beam therethrough.

5 Claims, 13 Drawing Sheets

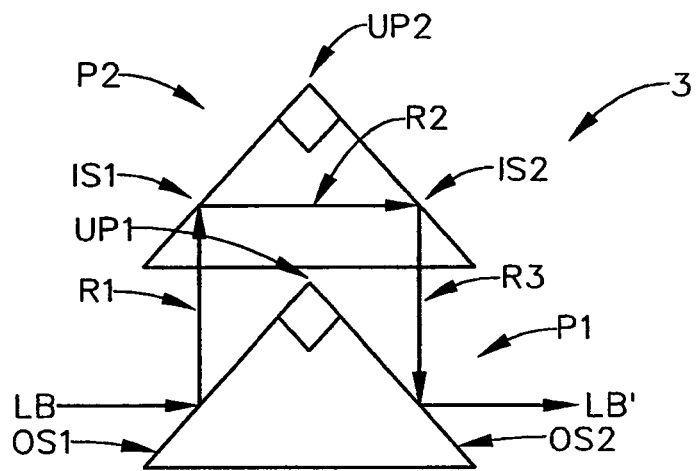
FIG. 3j₁
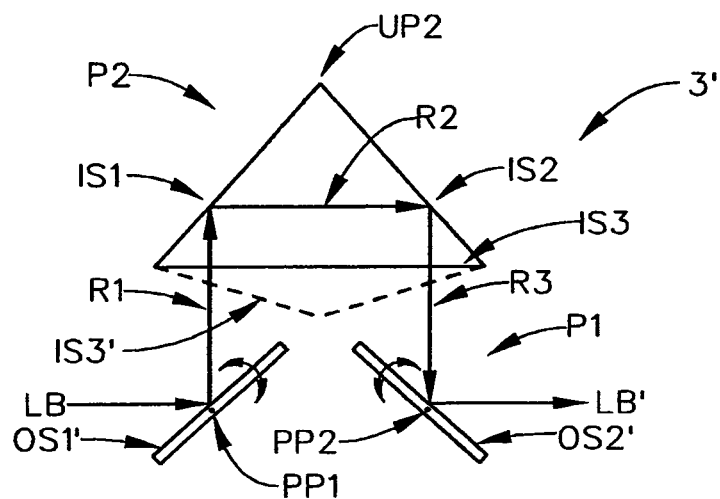
FIG. 3j₂
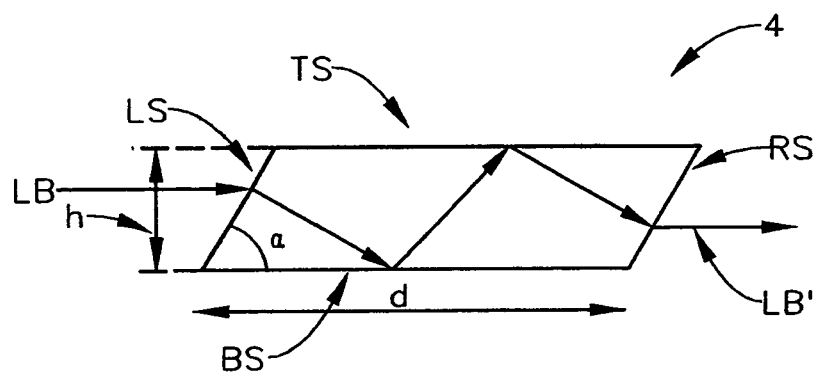
FIG. 3k

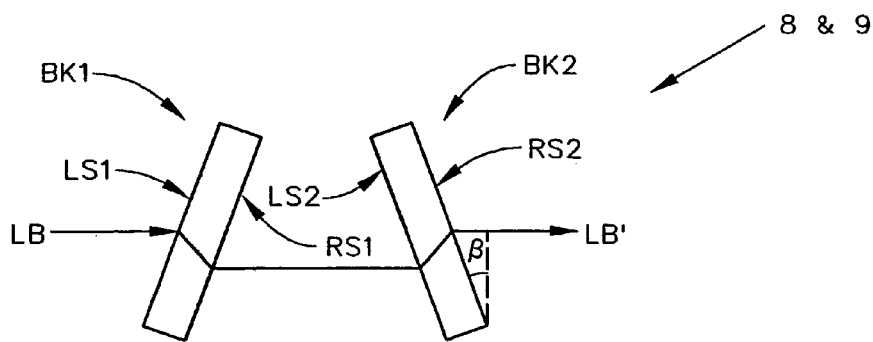
FIG. 3n₁
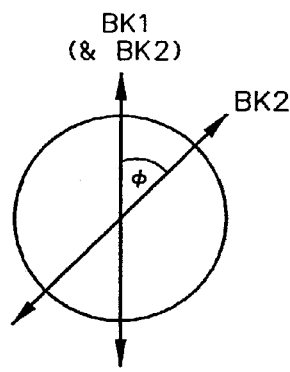
FIG. 3n₂
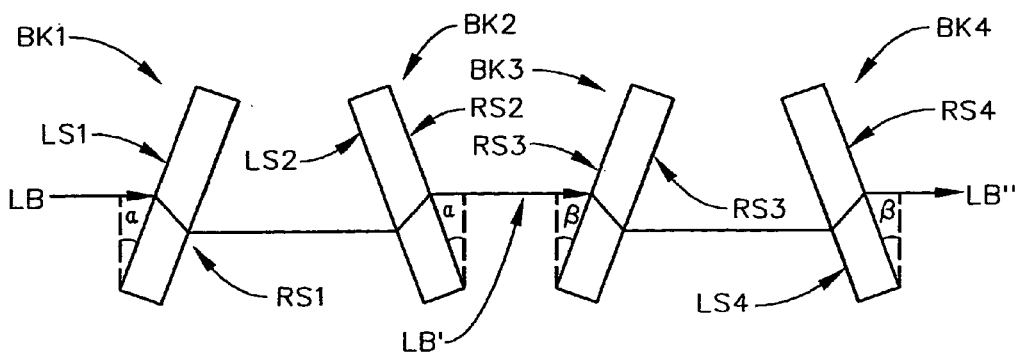
FIG. 3o₁

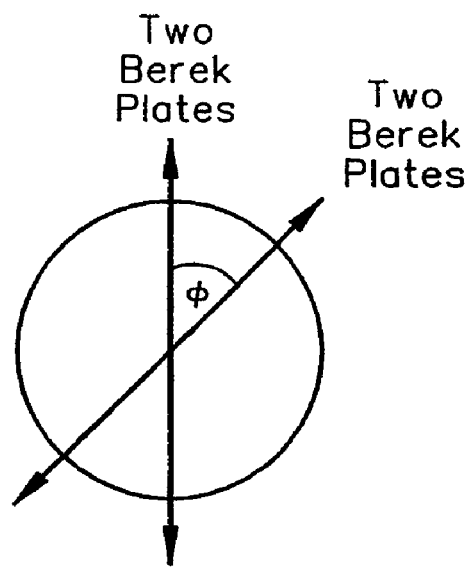
FIG. 3o₂
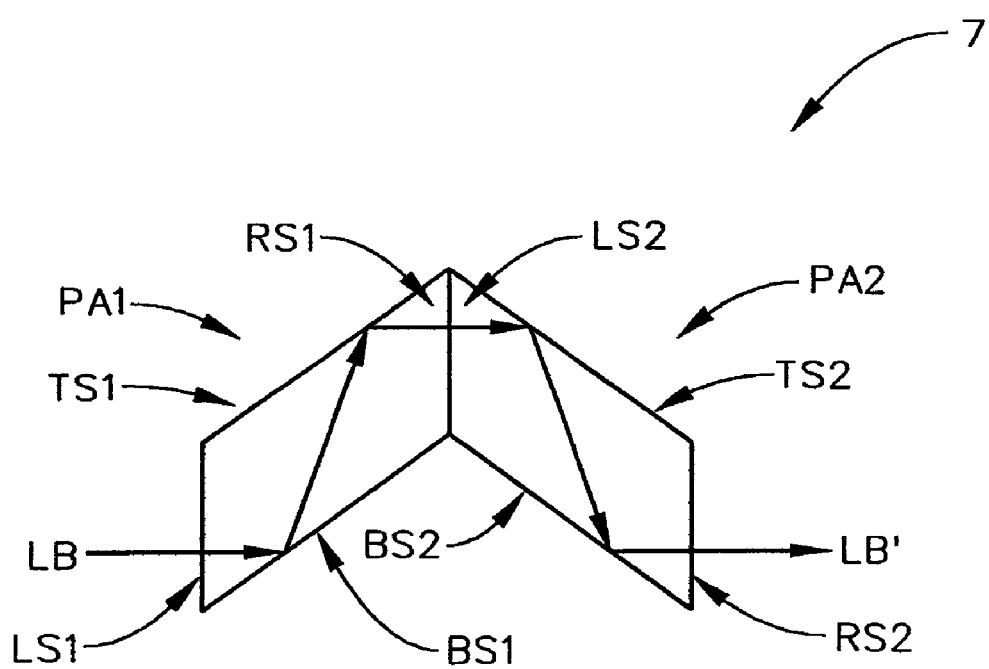
FIG. 3p

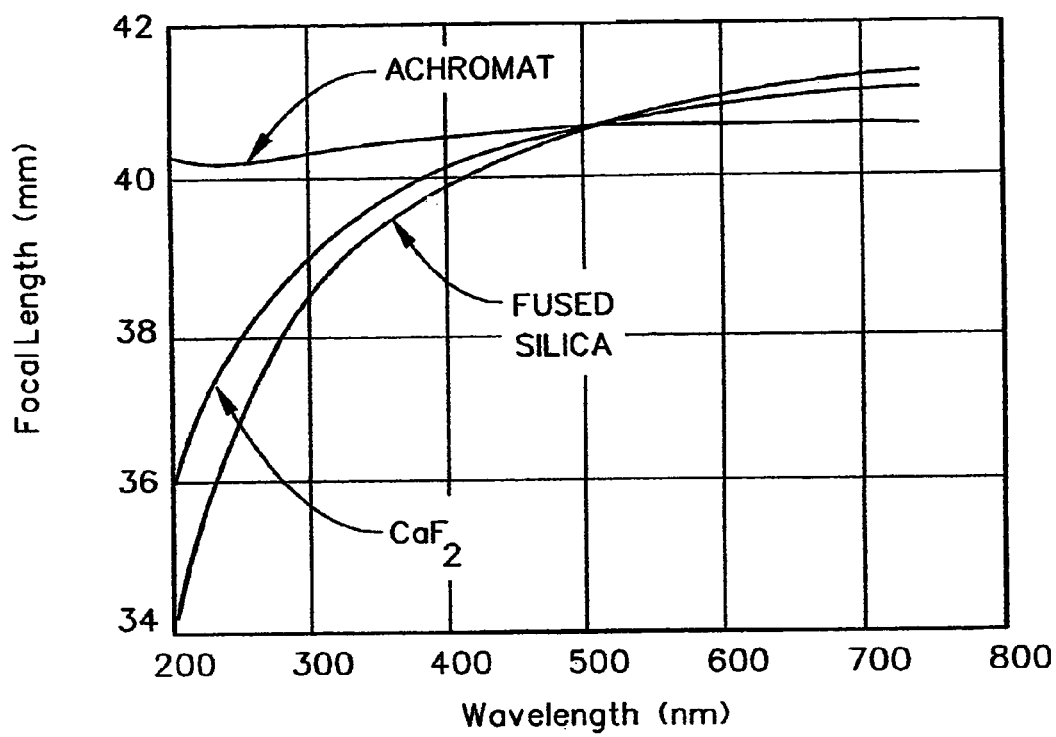
FIG. 7a1
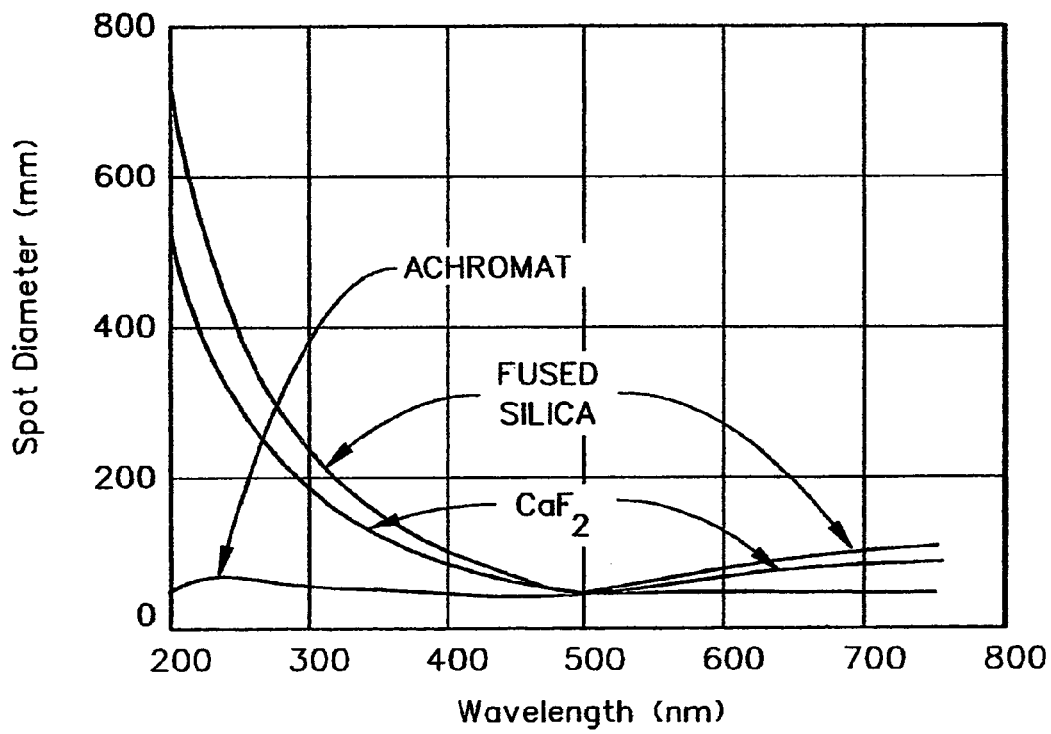
FIG. 7a2

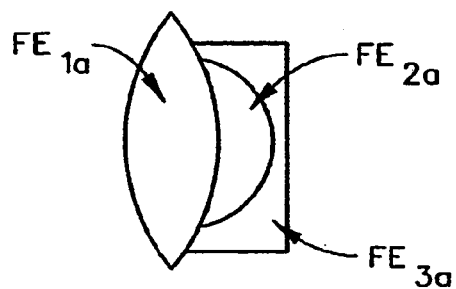
FIG. 7a₃
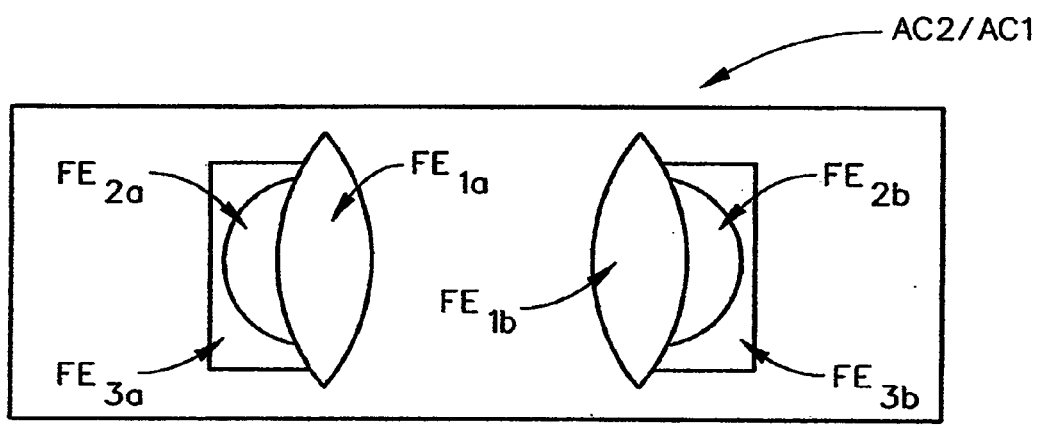
FIG. 7a₄
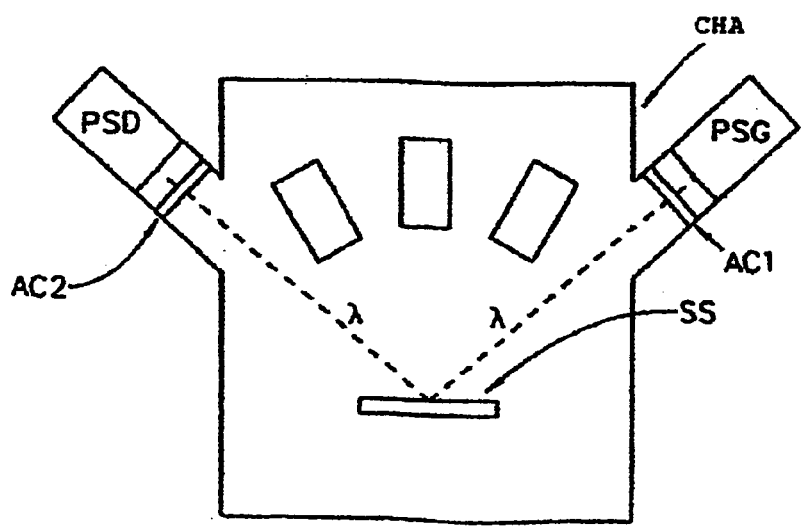
FIG. 8

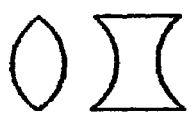 
FIG. 7a5      FIG. 7a6
   
FIG. 7a7   FIG. 7a8   FIG. 7a9   FIG. 7a10
 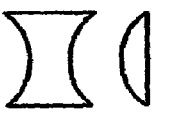  
FIG. 7a11   FIG. 7a12   FIG. 7a13   FIG. 7a14
 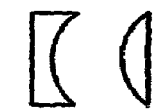 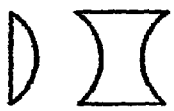 
FIG. 7a15   FIG. 7a16   FIG. 7a17   FIG. 7a18
   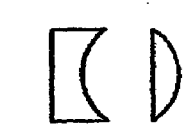
FIG. 7a19   FIG. 7a20   FIG. 7a21   FIG. 7a22
C   D   C   D              C   D   D   C
FIG. 7a23                  FIG. 7a24
D   C   D   C              D   C   C   D
FIG. 7a25                  FIG. 7a26

ROTATING OR ROTATABLE COMPENSATOR SPECTROSCOPIC ELLIPSOMETER SYSTEM INCLUDING MULTIPLE ELEMENT LENSES

This application is a Continuation-in-Part of application Ser. No. 10/034,800 Filed Dec. 28, 2001 now U.S. Pat. No. 6,822,738 and of application Ser. No. 09/583,229 Filed May 30, 2000 now U.S. Pat. No. 6,804,004 and therevia of Ser. No. 09/162,217 Filed Sep. 29, 1998 (now U.S. Pat. No. 6,034,777), of Ser. No. 09/033,694 Filed Mar. 3, 1998 (now U.S. Pat. No. 5,963,327); of Ser. No. 09/144,764 Filed Aug. 31, 1998 (now U.S. Pat. No. 5,969,818), of Ser. No. 09/419,794 Filed Oct. 18, 1999, and of Ser. No. 09/144,764 Filed Aug. 31, 1998 and therevia Claims benefit of Provisional 60/094,104 Filed Jul. 24, 1998.

This application further is a Continuation-in-Part of Copending application Ser. No. 10/699,540 Filed Nov. 1, 2003 and therevia of Copending application Ser. No. 09/945,962 Filed Sep. 4, 2001, application Ser. No. 09/517,125 Filed Feb. 29, 2000, and therevia of application Ser. No. 09/246,888 filed Feb. 8, 1999, (now U.S. Pat. No. 6,084,675). Further, via the Ser. No. 09/246,888 application, this application is a Continuation-In-Part of application Ser. No. 08/912,211 filed Aug. 15, 1997, (now U.S. Pat. No. 5,872,630), which was a CIP from application Ser. No. 08/530,892 filed Sep. 20, 1995, (now U.S. Pat. No. 5,666,201); and is a CIP of application Ser. No. 08/618,820 filed Mar. 20, 1996, (now U.S. Pat. No. 5,706,212). This application is further a CIP of application Ser. No. 09/225,118, Jan. 4, 1999 (now U.S. Pat. No. 6,084,674); Ser. No. 09/223,822, Jan. 4, 1999 (now U.S. Pat. No. 6,118,537); Ser. No. 09/232,257, Jan. 19, 1999 (now U.S. Pat. No. 6,141,102); Ser. No. 09/225,371, Jan. 4, 1999 (now U.S. Pat. No. 6,100,981); Ser. No. 09/225,076, Jan. 4, 1999 (now U.S. Pat. No. 5,963,325), which applications depend from application Ser. No. 08/997,311 filed Dec. 23, 1997, (now U.S. Pat. No. 5,946,098).

This application also Claims benefit of Provisional Application Ser. No. 60/527,554, Filed Dec. 6, 2003; and 60/527,638 Filed Dec. 8, 2003.

TECHNICAL FIELD

The present invention relates to ellipsometer systems, and more particularly to ellipsometer systems comprising transmissive rotating or stepwise rotatable compensators for continuously or step-wise varying polarization states and further comprising transmissive multi-element lens focusing of a spectroscopic electromagnetic beam into a small, chromatically relatively undispersed area spot on a material system. The ellipsometer system optionally is present in an environmental control chamber.

BACKGROUND

The practice of ellipsometry is well established as a non-destructive approach to determining characteristics of sample systems, and can be practiced in real time. The topic is well described in a number of publications, one such publication being a review paper by Collins, titled "Automatic Rotating Element Ellipsometers: Calibration, Operation and Real-Time Applications", Rev. Sci. Instrum., 61(8) (1990).

In general, modern practice of ellipsometry typically involves causing a spectroscopic beam of electromagnetic radiation, in a known state of polarization, to interact with a sample system at least one angle of incidence with respect to a normal to a surface thereof, in a plane of incidence. (Note, a plane of incidence contains both a normal to a surface of an investigated sample system and the locus of said beam of electromagnetic radiation). Changes in the polarization state of said beam of electromagnetic radiation which occur as a result of said interaction with said sample system are indicative of the structure and composition of said sample system. The practice of ellipsometry further involves proposing a mathematical model of the ellipsometer system and the sample system investigated by use thereof, and experimental data is then obtained by application of the ellipsometer system. This is typically followed by application of a square error reducing mathematical regression to the end that parameters in the mathematical model which characterize the sample system are evaluated, such that the obtained experimental data, and values calculated by use of the mathematical model, are essentially the same.

A typical goal in ellipsometry is to obtain, for each wavelength in, and angle of incidence of said beam of electromagnetic radiation caused to interact with a sample system, sample system characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$), caused by interaction with said sample system. The basic equation relating PSI and DELTA is:

$$\rho = rp/rs = \text{Tan}(\Psi)\exp(i\Delta)$$

As alluded to, the practice of ellipsometry requires that a mathematical model be derived and provided for a sample system and for the ellipsometer system being applied. In that light it must be appreciated that an ellipsometer system which is applied to investigate a sample system is, generally, sequentially comprised of:

a. a Source of a beam electromagnetic radiation;
b. a Polarizer element;
c. optionally a compensator element;
d. (additional element(s));
e. a sample system;
f. (additional element(s));
g. optionally a compensator element;
h. an Analyzer element; and
i. a Spectroscopic Detector System.

Each of said components b.–i. must be accurately represented by a mathematical model of the ellipsometer system along with a vector which represents a beam of electromagnetic radiation provided from said source of a beam electromagnetic radiation, Identified in a. above)

Various conventional ellipsometer configurations provide that a Polarizer, Analyzer and/or Compensator(s) can be rotated during data acquisition, and are describe variously as Rotating Polarizer (RPE), Rotating Analyzer (RAE) and Rotating Compensator (RCE) Ellipsometer Systems. As described elsewhere in this Specification, the present invention provides that no element must be continuously rotated during data acquisition but rather that a sequence of discrete polarization states can be imposed during data acquisition. This approach allows eliminating many costly components from conventional rotating element ellipsometer systems, and, hence, production of an "Ultra-Low-Complexity" ellipsometer system. It is noted, that nulling ellipsometers also exist in which elements therein are rotatable in use, rather than rotating. Generally, use of a nulling ellipsometer system involves imposing a linear polarization state on a beam of electromagnetic radiation with a polarizer, causing the resulting polarized beam of electromagnetic radiation to interact with a sample system, and then adjusting an analyzer to an azimuthal azimuthal angle which effectively cancels out the beam of electromagnetic radiation which proceeds past the sample system. The azimuthal angle of the analyzer at which nulling occurs provides insight to properties of the sample system.

It is further noted that reflectometer systems are generally sequentially comprised of:
  a. a Source of a beam electromagnetic radiation;
  d. (optional additional element(s));
  e. a sample system;
  f. (optional additional element(s));
  i. a Spectroscopic Detector System;

and that reflectometer systems monitor changes in intensity of a beam of electromagnetic radiation caused to interact with a sample system. That is, the ratio of, and phase angle between, orthogonal components in a polarized beam are not of direct concern.

Continuing, in use, data sets can be obtained with an ellipsometer system configured with a sample system present, sequentially for cases where other sample systems are present, and where an ellipsometer system is configured in a straight-through configuration wherein a beam of electromagnetic radiation is caused to pass straight through the ellipsometer system without interacting with a sample system. Simultaneous mathematical regression utilizing multiple data sets can allow evaluation of sample system characterizing PSI and DELTA values over a range of wavelengths. The obtaining of numerous data sets with an ellipsometer system configured with, for instance, a sequence of sample systems present and/or wherein a sequential plurality of polarization states are imposed on an electromagnetic beam caused to interact therewith, can allow system calibration of numerous ellipsometer system variables.

Patents of which the Inventor is aware include those to Woollam et al, U.S. Pat. No. 5,373,359, Patent to Johs et al. U.S. Pat. No. 5,666,201 and Patent to Green et al., U.S. Pat. No. 5,521,706, and Patent to Johs et al., U.S. Pat. No. 5,504,582 are disclosed for general information as they pertain to ellipsometer systems.

Further Patents of which the Inventor is aware include U.S. Pat. Nos. 5,757,494 and 5,956,145 to Green et al., in which are taught a method for extending the range of Rotating Analyzer/Polarizer ellipsometer systems to allow measurement of DELTA'S near zero (0.0) and one-hundred-eighty (180) degrees, and the extension of modulator element ellipsometers to PSI'S of forty-five (45) degrees. Said Patents describes the presence of a variable, transmissive, bi-refringent component which is added, and the application thereof during data acquisition to enable the identified capability.

A Patent to Thompson et al. U.S. Pat. No. 5,706,212 is also disclosed as it teaches a mathematical regression based double Fourier series ellipsometer calibration procedure for application, primarily, in calibrating ellipsometers system utilized in infrared wavelength range. Bi-refringent, transmissive window-like compensators are described as present in the system thereof, and discussion of correlation of retardations entered by sequentially adjacent elements which do not rotate with respect to one another during data acquisition is described therein.

A Patent to He et al., U.S. Pat. No. 5,963,327 is disclosed as it describes an ellipsometer system which enables providing a polarized beam of electromagnetic radiation at an oblique angle-of-incidence to a sample system in a small spot area.

A Patent to Johs et al., U.S. Pat. No. 5,872,630 is disclosed as it describes an ellipsometer system in which an analyzer and polarizer are maintained in a fixed in position during data acquisition, while a compensator is caused to continuously rotate.

Patent to Dill et al., U.S. Pat. No. 4,953,232 is disclosed as it describes a rotating compensator ellipsometer system.

Patents co-owned with this Application, which Patents Claim various Compensator Designs recited in Claims herein, and which Patents are incorporated hereinto by reference are:
  U.S. Pat. No. 5,946,098 to Johs et al.;
  U.S. Pat. No. 5,963,325 to Johs et al.;
  U.S. Pat. No. 6,084,674 to Johs et al.;
  U.S. Pat. No. 6,084,675 to Herzinger et al.;
  U.S. Pat. No. 6,100,981 to Johs et al.;
  U.S. Pat. No. 6,118,537 to Johs et al.;
  U.S. Pat. No. 6,141,102 to Johs et al.

Patents cited in examination of said Patents included U.S. Pat. No. 4,556,292 to Mathyssek et al. and U.S. Pat. No. 5,475,525 to Tournois et al.

A Patent to Coates et al., U.S. Pat. No. 4,826,321 is disclosed as it describes applying a reflected monochromatic beam of plane polarized electromagnetic radiation at a Brewster angle of incidence to a sample substrate to determine the thickness of a thin film thereupon. This Patent also describes calibration utilizing two sample substrates, which have different depths of surface coating.

Other Patents which describe use of reflected electromagnetic radiation to investigate sample systems are U.S. Pat. Nos. RE 34,783, 4,373,817, and 5,045,704 to Coates; and U.S. Pat. No. 5,452,091 to Johnson.

A Patent to Biork et al., U.S. Pat. No. 4,647,207 is disclosed as it describes an ellipsometer system which has provision for sequentially positioning a plurality of reflective polarization state modifiers in a beam of electromagnetic radiation. While said 207 Patent mentions investigating a sample system in a transmission mode, no mention or suggestion is found for utilizing a plurality of transmitting polarization state modifiers, emphasis added. U.S. Pat. Nos. 4,210,401; 4,332,476 and 4,355,903 are also identified as being cited in the 207 Patent. It is noted that systems as disclosed in these Patents, (particularly in the 476 Patent), which utilize reflection from an element to modify a polarization state can, that if such an element is an essential duplicate of an investigated sample and is rotated ninety degrees therefrom, then the effect of the polarization state modifying element on the electromagnetic beam effect is extinguished by the sample.

A Patent to Mansuripur et al., U.S. Pat. No. 4,838,695 is disclosed as it describes an apparatus for measuring reflectivity.

Patents to Rosencwaig et al., U.S. Pat. Nos. 4,750,822 and 5,595,406 are also identified as they describe systems which impinge electromagnetic beams onto sample systems at oblique angles of incidence. The 406 Patent provides for use of multiple wavelengths and multiple angles of incidence. For similar reasons U.S. Pat. No. 5,042,951 to Gold et al. is also disclosed.

A Patent to Osterberg, U.S. Pat. No. 2,700,918 describes a microscope with variable means for increasing the visibility of optical images, partially comprised of discrete bi-refringent plates which can be positioned in the pathway between an eyepiece and an observed object. Other Patents identified in a Search which identified said 918 Patent are U.S. Pat. No. 3,183,763 to Koester; U.S. Pat. No. 4,105,338 to Kuroha; U.S. Pat. No. 3,992,104 to Watanabe and a Russian Patent, No. SU 1518728. Said other Patents are not believed to be particularly relevant, however.

A U.S. Pat. No. 5,329,357 to Bernoux et al. is also identified as it Claims use of fiber optics to carry electromagnetic radiation to and from an ellipsometer system which has at least one polarizer or analyzer which rotates during data acquisition. It is noted that if both the polarizer and analyzer are stationary during data acquisition that this Patent is not controlling where electromagnetic radiation carrying fiber optics are present.

A Patent to Chen et al., U.S. Pat. No. 5,581,350, is disclosed as it describes a method for regression calibration of ellipsometers.

As present invention preferred practice is to utilize a spectroscopic source of electromagnetic radiation with a relatively flat spectrum over a large range of wavelengths U.S. Pat. No. 6,628,917 to Johs is disclosed. Patents relevant thereto include U.S. Pat. No. 5,179,462 to Kageyama et al. is identified as it provides a sequence of three electromagnetic beam combining dichroic mirrors in an arrangement which produces an output beam of electromagnetic radiation that contains wavelengths from each of four sources of electromagnetic radiation. Each electromagnetic beam combining dichroic mirror is arranged so as to transmit a first input beam of electromagnetic radiation, comprising at least a first wavelength content, therethrough so that it exits a second side of said electromagnetic beam combining dichroic mirror, and to reflect a second beam of electromagnetic radiation, comprising an additional wavelength content, from said second side of said electromagnetic beam combining dichroic mirror in a manner that a single output beam of electromagnetic radiation is formed which contains the wavelength content of both sources of electromagnetic radiation. The sources of electromagnetic radiation are described as lasers in said 462 Patent. Another U.S. Pat. No. 5,296,958 to Roddy et al., describes a similar system which utilizes Thompson Prisms to similarly combine electromagnetic beams for laser source. U.S. Pat. Nos. 4,982,206 and 5,113,279 to Kessler et al. and Hanamoto et al. respectively, describe similar electromagnetic electromagnetic beam combination systems in laser printer and laser beam scanning systems respectively. Another U.S. Pat. No. 3,947,688 to Massey, describes a method of generating tunable coherent ultraviolet light, comprising use of an electromagnetic electromagnetic beam combining system. A Patent to Miller et al., U.S. Pat. No. 5,155,623, describes a system for combining information beams in which a mirror comprising alternating regions of transparent and reflecting regions is utilized to combine transmitted and reflected beams of electromagnetic radiation into a single output beam. A Patent to Wright, U.S. Pat. No. 5,002,371 is also mentioned as describing a beam splitter system which operates to separate "P" and "S" orthogonal components in a beam of polarized electromagnetic radiation.

Patents identified in a Search specifically focused on the use of lenses, preferrably achromatic, in ellipsometry and related systems are:

U.S. Pat. Nos. 5,877,859 and 5,798,837 to Aspnes et al.;
U.S. Pat. No. 5,333,052 to Finarov;
U.S. Pat. No. 5,608,526 to Piwonka-Corle et al.;
U.S. Pat. No. 5,793,480 to Lacy et al.;
U.S. Pat. Nos. 4,636,075 and 4,893,932 to Knollenberg; and
U.S. Pat. No. 4,668,860 to Anthon.

The most relevant Patent found is U.S. Pat. No. 5,917,594 to Norton. However, the system disclosed therein utilizes a spherical mirror to focus an electromagnetic beam onto the surface of a sample in the form of a small spot. Said system further develops both reflection and transmission signals via application of reflective means and of reflection and transmission detectors. The somewhat relevant aspect of the 594 Patent system is that a positive lens and a negative meniscus lens are combined and placed into the pathway of the electromagnetic beam prior to its reflection from a focusing spherical mirror. The purpose of doing so is to make the optical system, as a whole, essentially achromatic in the visible wavelength range, and even into the ultraviolet wavelength range. It is further stated that the power of the combined positive lens and negative meniscus lens is preferrably zero. It is noted that, as described elsewhere in this Specification, said 594 Patent lens structure, positioning in the 594 Patent system, and purpose thereof are quite distinct from the present invention lens structure and application to focus a beam of electromagnetic radiation. In particular, note that the 594 Patent lens is not applied to directly focus and/or recollimate a beam of electromagnetic radiation onto a sample system, as do the lenses in the present invention. And, while the present invention could utilize a meniscus lens in an embodiment thereof, the 594 Patent specifically requires and employs a negative meniscus lens to correct for spherical aberabtions caused by off-axis reflection from a spherical mirror, in combination with a positive lens to correct for achromatic aberation introduced by said negative meniscus lens. Further, the present invention system does not require reflection means be present in the path of an electromagnetic beam after its passage through the focusing lens thereof and prior to interacting with a sample system, as does the system in the 594 Patent wherein a focusing spherical mirror is functionally required.

In addition to the identified Patents, certain Scientific papers are also identified.

A paper by Johs, titled "Regression Calibration Method for Rotating Element Ellipsometers", Thin Solid Films, 234 (1993) is also disclosed as it describes a mathematical regression based approach to calibrating ellipsometer systems.

Another paper, by Gottesfeld et al., titled "Combined Ellipsometer and Reflectometer Measurements of Surface Processes on Nobel Metals Electrodes", Surface Sci., 56 (1976), is also identified as describing the benefits of combining ellipsometry and reflectometry.

A paper by Smith, titled "An Automated Scanning Ellipsometer", Surface Science, Vol. 56, No. 1. (1976), is also mentioned as it describes an ellipsometer system which does not require any moving, (eg. rotating), elements during data acquisition.

Four additional papers by Azzam and Azzam et al. are also identified and are titled:

"Multichannel Polarization State Detectors For Time-Resolved Ellipsometry", Thin Solid Film, 234 (1993); and "Spectrophotopolarimeter Based On Multiple Reflections In A Coated Dielectric Slab", Thin Solid Films 313 (1998); and "General Analysis And Optimization Of The Four-Detector Photopolarimeter", J. Opt. Soc. Am., A, Vol. 5, No. 5 (May 1988); and "Accurate Calibration Of Four-Detector Photopolarimeter With Imperfect Polarization Optical Elements", J. Opt. Soc. Am., Vol. 6, No. 10, (October 1989);

Papers of interest in the area by Azzam & Bashara include one titled "Unified Analysis of Ellipsometry Errors Due to Imperfect Components Cell-Window Birifringence, and Incorrect Azimuth Angles", J. of the Opt. Soc. Am. Vol 61, No. 5, (May 1971); and one titled "Analysis of Systematic Errors in Rotating-Analyzer Ellipsometers", J. of the Opt. Soc. Am., Vol. 64, No. 11, (November 1974).

Another paper by Straaher et al, titled "The Influence of Cell Window Imperfections on the Calibration and Measured Data of Two Types of Rotating Analyzer Ellipsometers", Surface Sci., North Holland, 96, (1980), describes a graphical method for determining a plane of incidence in the presence of windows with small retardation.

A paper by Jones titled "A New Calculus For The Treatment Of Optical Systems", J.O.S.A., Voil. 31, (July 1941), is also identified as it describes the characterizing of multiple lens elements which separately demonstrate birefringence, as a single lens, (which can demonstrate reduced birefringence).

Finally, a paper which is co-authored by inventors herein is titled "In Situ Multi-Wavelength Ellipsometric Control of Thickness and Composition of Bragg Reflector Structures", by Herzinger, Johs, Reich, Carpenter & Van Hove, Mat. Res. Soc. Symp. Proc., Vol. 406, (1996) is also disclosed.

Even in view of relevant prior art, there remains need for a spectroscopic ellipsometer system which:
  presents with stationary polarizer and analyzer during data acquisition;
  utilizes a plurality of transmissive step-wise rotatable or rotating compensator means to effect a plurality of sequential polarization states during said data acquisition;
  which includes at least one multi-element lens; and a source of spectroscopic electromagnetic radiation and/or a spectroscopic multi-element detector system therewith.

The present invention provides a system with the identified attributes.

DISCLOSURE OF THE INVENTION

The present invention is, in the first instance, a spectroscopic ellipsometer system basically comprising:
  a source of polychromatic electromagnetic radiation;
  a polarizer which is fixed in position during data acquisition;
  a stage for supporting a sample system;
  an analyzer which is fixed in position during data acquisition; and
  a multi-element spectroscopic detector system.

In addition, the present invention ellipsometer system further comprises at least one means for continuously or discretely, sequentially, modifying a polarization state of a beam of electromagnetic radiation through a plurality of polarization states. The at least one means for continuously or discretely, sequentially, modifying a polarization state of a beam of electromagnetic radiation through a plurality of polarization states, is positioned between said polarizer and said stage for supporting a sample system, and/or and between said stage for supporting a sample system and said analyzer, and so that said beam of electromagnetic radiation transmits through a polarization state modifier element thereof in use. The present invention at least one means for continuously or discretely, sequentially, modifying a polarization state of a beam of electromagnetic radiation through a plurality of polarization states comprises a compensator which is mounted to allow rotation about the locus of a beam of electromagnetic radiation caused to pass therethrough.

Said spectroscopic ellipsometer system further comprises at least one multiple element lens present at least one location selected from the group consisting of:
  between said polarizer and said stage for supporting a sample system; and
  between said stage for supporting a sample system and said analyzer;

and positioned so that said beam of electromagnetic radiation transmits therethrough in use.

The present invention is further a combination spectroscopic reflectometer/ellipsometer system basically comprising:
  a source of polychromatic electromagnetic radiation;
  a stage for supporting a sample system;
  a multi-element spectroscopic detector system.

The combination spectroscopic reflectometer/ellipsometer system further comprises, in the ellipsometer system portion thereof, a polarizer, (which is fixed in position during data acquisition), present between the source of polychromatic electromagnetic radiation and the stage for supporting a sample system, and an analyzer, (which is fixed in position during data acquisition), present between the stage for supporting a sample system and the multi-element spectroscopic detector system. The ellipsometer system also comprises at least one means for discretely, sequentially, modifying a polarization state of a beam of electromagnetic radiation through a plurality of polarization states present between said polarizer and said stage for supporting a sample system, and/or between said stage for supporting a sample system and said analyzer, and positioned so that said beam of electromagnetic radiation transmits through a polarization state modifier element therein during use.

Additionally, the combination spectroscopic reflectometer/ellipsometer system is configured such that a polychromatic beam of electromagnetic radiation provided by said source of polychromatic electromagnetic radiation can, optionally, be directed to interact with a sample system present on said stage for supporting a sample system without any polarization state being imposed thereupon, and such that a polychromatic beam of electromagnetic radiation also provided by said source of polychromatic electromagnetic radiation can be, optionally simultaneously, directed to interact with a sample system present on said stage for supporting a sample system after a polarization state has been imposed thereupon. The polychromatic beam of electromagnetic radiation without any polarization state imposed thereupon, when directed to interact with a sample system present on said stage for supporting a sample system, is typically caused to approach said sample system at an oblique angle-of-incidence which is between a sample system Brewster angle and a normal to the surface of the sample system. Further, the polychromatic beam of electromagnetic radiation provided by said source of polychromatic electromagnetic radiation upon which a polarization state has been imposed, is typically directed to interact with a sample system present on said stage for supporting a sample system at an angle near the Brewster angle of the sample system being investigated. Either, or both, the polychromatic beam(s) of electromagnetic radiation provided by said source of polychromatic electromagnetic radiation, upon which is imposed a polarization state or upon which no polarization state is imposed, is preferably directed to interact with a sample system present on said stage for supporting a sample system via a fiber optic means.

While the present invention can utilize essentially any Compensator such as:
  Berek-type with optical axis essentially perpendicular to a surface thereof;
  non-Berek-type with an optical axis essentially parallel to a surface thereof;
  zero-order wave plate;
  zero-order waveplate constructed from two multiple order waveplates;
  a sequential plurality of zero-order waveplates, each constructed each from a plurality of multiple order waveplates;
  rhomb;
  polymer;
  achromatic crystal; and
  pseudo-achromatic.

preferred embodiments of the present invention provides that at least one of said at least one compensator(s), which is mounted to allow continuous rotation or step-wise rotation about the locus of a beam of electromagnetic radiation caused to pass therethrough, be selected from the group consisting of:
  a single element compensator;
  a multiple element compensator;
  a compensator system comprised of at least two per se. zero-order waveplates (MOA) and (MOB), said per se. zero-order waveplates (MOA) and (MOB) having their respective fast axes rotated to a position offset from zero or ninety degrees with respect to one another, with a nominal value being forty-five degrees;
  a compensator system comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position at a nominal forty-five degrees to the fast axes (FAA1) and (FAB1), respectively, of the multiple order waveplates (MOA1) and (MOB1) in said first effective zero-order waveplate (ZO1);
  a compensator system comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position away from zero or ninety degrees with respect to the fast axes (FAA1) and (FAB1), respectively, of the multiple order waveplates (MOA1) and (MOB1) in said first effective zero-order waveplate (ZO1);
  a compensator system comprised of at least one zero-order waveplate, ((MOA) or (MOB)), and at least one effective zero-order waveplate, ((ZO2) or (ZO1) respectively), said effective zero-order wave plate, ((ZO2) or (ZO1)), being comprised of two multiple order waveplates which are combined with the fast axes thereof oriented at a nominal ninety degrees to one another, the fast axes of the multiple order waveplates in said effective zero-order wave plate, ((ZO2) or (ZO1)), being rotated to a position away from zero or ninety degrees with respect to the fast axis of the zero-order waveplate, ((MOA) or (MOB));

where the identifiers are shown in FIGS. 3e–3i.

Additional compensator systems, previously disclosed in patent application Ser. No. 08/997,311, (now U.S. Pat. No. 5,946,098), and CIP's therefrom, which are specifically within the scope of the invention and can be included in the selection group are:
  a compensator system comprised of a first triangular shaped element, which as viewed in side elevation presents with first and second sides which project to the left and right and downward from an upper point, which first triangular shaped element first and second sides have reflective outer surfaces; said retarder system further comprising a second triangular shaped element which as viewed in side elevation presents with first and second sides which project to the left and right and downward from an upper point, said second triangular shaped element being made of material which provides reflective interfaces on first and second sides inside thereof; said second triangular shaped element being oriented with respect to the first triangular shaped element such that the upper point of said second triangular shaped element is oriented essentially vertically directly above the upper point of said first triangular shaped element; such that in use an input electromagnetic beam of radiation caused to approach one of said first and second sides of said first triangular shaped element along an essentially horizontally oriented locus, is caused to externally reflect from an outer surface thereof and travel along a locus which is essentially upwardly vertically oriented, then enter said second triangular shaped element and essentially totally internally reflect from one of said first and second sides thereof, then proceed along an essentially horizontal locus and essentially totally internally reflect from the other of said first and second sides and proceed along an essentially downward vertically oriented locus, then externally reflect from the other of said first and second sides of said first triangular shaped elements and proceed along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;
  a compensator system comprised of, as viewed in upright side elevation, first and second orientation adjustable mirrored elements which each have reflective surfaces; said compensator/retarder system further comprising a third element which, as viewed in upright side elevation, presents with first and second sides which project to the left and right and downward from an upper point, said third element being made of material which provides reflective interfaces on first and second sides inside thereof; said third element being oriented with respect to said first and second orientation adjustable mirrored elements such that in use an input electromagnetic beam of radiation caused to approach one of said first and second orientation adjustable mirrored elements along an essentially horizontally oriented locus, is caused to externally reflect therefrom and travel along a locus which is essentially upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second orientation adjustable mirrored elements and proceed along an essentially horizontally oriented propagation direction locus which is essentially undeviated and undisplaced from the essentially horizontally oriented propagation direction locus of said input beam of essentially horizontally oriented electromagnetic radiation even when said compensator/retarder is caused to rotate; with a result being that retardation is entered between orthogonal components of said input electromagnetic beam of radiation;

a compensator system comprised of a parallelogram shaped element which, as viewed in side elevation, has top and bottom sides parallel to one another, both said top and bottom sides being oriented essentially horizontally, said retarder system also having right and left sides parallel to one another, both said right and left sides being oriented at an angle to horizontal, said retarder being made of a material with an index of refraction greater than that of a surrounding ambient; such that in use an input beam of electromagnetic radiation caused to enter a side of said retarder selected from the group consisting of: (right and left), along an essentially horizontally oriented locus, is caused to diffracted inside said retarder system and follow a locus which causes it to essentially totally internally reflect from internal interfaces of both said top and bottom sides, and emerge from said retarder system from a side selected from the group consisting of (left and right respectively), along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of first and second triangular shaped elements, said first triangular shaped element, as viewed in side elevation, presenting with first and second sides which project to the left and right and downward from an upper point, said first triangular shaped element further comprising a third side which is oriented essentially horizontally and which is continuous with, and present below said first and second sides; and said second triangular shaped element, as viewed in side elevation, presenting with first and second sides which project to the left and right and upward from an upper point, said second triangular shaped element further comprising a third side which is oriented essentially horizontally and which is continuous with, and present above said first and second sides; said first and second triangular shaped elements being positioned so that a rightmost side of one of said first and second triangular shaped elements is in contact with a leftmost side of the other of said first and second triangular shaped elements over at least a portion of the lengths thereof; said first and second triangular shaped elements each being made of material with an index of refraction greater than that of a surrounding ambient; such that in use an input beam of electromagnetic radiation caused to enter a side of a triangular shaped element selected from the group consisting of: (first and second), not in contact with said other triangular shape element, is caused to diffracted inside said retarder and follow a locus which causes it to essentially totally internally reflect from internal interfaces of said third sides of each of said first and second triangular shaped elements, and emerge from a side of said triangular shaped element selected from the group consisting of: (second and first), not in contact with said other triangular shape element, along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of a triangular shaped element, which as viewed in side elevation presents with first and second sides which project to the left and right and downward from an upper point, said retarder system further comprising a third side which is oriented essentially horizontally and which is continuous with, and present below said first and second sides; said retarder system being made of a material with an index of refraction greater than that of a surrounding ambient; such that in use a an input beam of electromagnetic radiation caused to enter a side of said retarder system selected from the group consisting of: (first and second), along an essentially horizontally oriented locus, is caused to diffracted inside said retarder system and follow a locus which causes it to essentially totally internally reflect from internal interface of said third sides, and emerge from said retarder from a side selected from the group consisting of (second and first respectively), along an essentially horizontally oriented locus which is undeviated and undisplaced from the essentially horizontally oriented locus of said input beam of essentially horizontally oriented electromagnetic radiation even when said retarder system is caused to rotate; with a result being that retardation is entered between orthogonal components of said input electromagnetic beam of radiation; and a compensator system comprised of first and second Berek-type retarders which each have an optical axes essentially perpendicular to a surface thereof, each of which first and second Berek-type retarders has a fast axis, said fast axes in said first and second Berek-type retarders being oriented in an orientation selected from the group consisting of: (parallel to one another and other than parallel to one another); said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder;

such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation even when said retarder system is caused to rotate; with a result being that retardation is entered between orthogonal components of said input electromagnetic beam of radiation;

a compensator system comprised of first and second Berek-type retarders which each have an optical axes essentially perpendicular to a surface thereof, each of which first and second Berek-type retarders has a fast axis, said fast axes in said first and second Berek-type retarders being oriented other than parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation, said compensator system further comprising third and forth Berek-type retarders which each have an optical axes essentially perpendicular to a surface thereof, each of which third and forth Berek-type retarders has a fast axis, said fast axes in said third and forth Berek-type retarders being oriented other than parallel to one another, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation;

a compensator system comprised of first, second, third and forth Berek-type retarders which each have an optical axes essentially perpendicular to a surface thereof, each of which first and second Berek-type retarders has a fast axis, said fast axes in said first and second Berek-type retarders being oriented essentially parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation; each of which third and forth Berek-type retarders has a fast axis, said fast axes in said third and forth Berek-type retarders being oriented essentially parallel to one another but other than parallel to the fast axes of said first and second Berek-type retarders, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation;

said compensator causing essentially no deviation or displacement in a polychromatic beam of electromagnetic radiation caused to pass therethrough while caused to rotate.

It is to be appreciated that the present Application can apply Compensator(s) in a system which causes continuous rotation thereof during data acquisition, or steps a compensator through a series of discrete rotational positions, and holds it stationary while obtaining data. Further, while not required, the present invention benefits from Compensator(s) designed to provide relatively constant, achromatic Polarization State Modification effects over a Spectroscopic range of wavelengths.

Continuing, said at least one multiple element lens present at least one location selected from the group consisting of:
  between said polarizer and said stage for supporting a sample system; and
  between said stage for supporting a sample system and said analyzer;

and positioned so that said beam of electromagnetic radiation transmits therethrough in use typically comprises at least two elements which are made from different materials, such that in use the focal length for each wavelength in a range of wavelengths is within an acceptable range of focal lengths. Said at least one multi-element lens is characterized by a selection from the group consisting of:
  a) at least one thereof comprises:
    two sequentially oriented elements, one of said two sequentially oriented elements being of a shape and orientation which individually diverges a beam of electromagnetic radiation caused to pass therethrough, and the other being of a shape and orientation which individually converges a beam of electromagnetic radiation caused to pass therethrough,
      there being a region between said at least two elements such that, in use, a beam of electromagnetic radiation sequentially passes through one of said at least two elements, then said region therebetween, and then the other of said at least two elements before emerging as an effectively converged, focused, beam of electromagnetic radiation.
  b) at least one thereof comprises:
    a sequential combination of a bi-convex element and a bi-concave element.
  c) at least one thereof comprises:
    a sequential combination of a bi-concave element and a bi-convex element.
  d) at least one thereof comprises:
    a sequential combination of a bi-convex element and a plano-concave element with said concave side of said plano-concave element adjacent to said bi-convex element.
  e) at least one thereof comprises:
    a sequential combination of a bi-convex element and a plano-concave element with said essentially flat side of said plano-concave element being adjacent to said bi-convex element;
  f) at least one thereof comprises:
    a sequential combination of a plano-concave element and a bi-convex element with said essentially flat side of said plano-concave element adjacent to said bi-concave element;
  g) at least one thereof comprises:
    a sequential combination of a plano-concave element and bi-convex element with said concave side of said plano-concave element adjacent to said bi-convex element;
  h) at least one thereof comprises:
    a sequential combination of a plano-convex element and a bi-concave element with said essentially flat side of said plano-convex element adjacent to said bi-concave element;
  i) at least one thereof comprises:
    a sequential combination of a bi-concave element with a plano-convex element with said convex side of said plano-convex element adjacent to said bi-concave element;
  j) at least one thereof comprises:
    a sequential combination of a plano-concave element and a plano-convex element with the essentially flat side of said plano-concave element being adjacent to the convex side of the plano-convex element;
  k) at least one thereof comprises:
    a sequential combination of a plano-concave element and a plano-convex element with the essentially flat side of said planoconcave element being adjacent to the flat side of said plano-convex element;
  l) at least one thereof comprises:
    a sequential combination of a plano-convex element and a plano-concave element with the essentially flat side of said plano-convex element and the essentially flat side of said plano-concave element being adjacent to one another;
  m) at least one thereof comprises:
    a sequential combination of a plano-concave element and a plano-convex element with the concave side of said plano-concave element being adjacent to the convex side of the plano-convex element;
  n) at least one thereof comprises:
    a sequential combination of a plano-convex element bi-concave element with said convex side of said plano-convex element adjacent to said bi-concave element;
  o) at least one thereof comprises:
    a sequential combination of a bi-concave element and a plano-convex element with said essentially flat side of said plano-convex element adjacent to said bi-concave element;
  p) at least one thereof comprises:
    a sequential combination of a plano-convex element and a plano-concave element with said convex side of said plano-convex element adjacent to the concave side of the plano-concave element;
  q) at least one thereof comprises:
    a sequential combination of a plano-concave element and a plano-convex element with said essentially flat side of said plano-concave element being adjacent to the essentially convex side of the plano-convex element;
  r) at least one thereof comprises:
    a sequential combination of a plano-convex element and a plano-concave element with said convex side of said plano-convex element being adjacent to the essentially flat side of the plano-concave element;
  s) at least one thereof comprises:
    a sequential combination of a plano-concave element with a plano-convex element with the essentially flat side of said plano-convex element being adjacent to the concave side of said plano-concave element;

t) at least one thereof comprises:
  at least one of the input and output lenses comprises at least two sequentially oriented elements, and is characterized by being a selection from the group consisting of:
    a sequential combination of a converging element and a diverging element;
    a sequential combination of a diverging element and a converging element;
    a sequential combination of a converging element, a diverging element, a converging element and a diverging element;
    a sequential combination of a converging element, a diverging element, a diverging element and a converging element;
    a sequential combination of a diverging element, a converging element, a diverging element and a converging element;
    a sequential combination of a diverging element, a converging element, a converging element and a diverging element;
  includes a miniscus lens; and
  includes an aspherical lens;
u) at least one thereof comprises:
  two elements with a region therebetween, wherein said region between said at least two elements has the optical properties of a selection from the group consisting of:
    a void region; and
    a functional equivalent to a void region;
v) at least one thereof comprises:
  at least two elements which are made from different materials independently selected from the group consisting of:
    $CaF_2$;
    $BaF_2$;
    LiF;
    $MgF_2$;
    fused silica;
    a void region;
    a gas filled region;
    a liquid filled region; and
    a functional equivalent to a void region.

and wherein each of said at least two elements are individually selected to be made of different materials;
  w) at least one thereof is characterized by at least one selection from the group consisting of:
    a) the focal length is between forty and forty-one millimeters over a range of wavelengths of at least two-hundred to seven-hundred nanometers;
    b) the focal length varies by less than five (5%) percent over a range of wavelengths of between two-hundred and five-hundred nanometers; and
    c) the spot diameter at the focal length is less than seventy-five microns over a range of wavelengths of at least two-hundred to seven-hundred nanometers;
  x) at least one thereof comprises:
    an element made of a selection from the group consisting of:
      $CaF_2$; and
      fused silica;
  y) at least one thereof:
    is made of two elements, one of said elements being made of Fused Silica and the other of $CaF_2$;
  z) at least one thereof comprises:
    a converging element selected from the group consisting of:
      a positive miniscus;
      an asymmetric convex;
  and/or a diverging element selected from the group consisting of:
    a negative miniscus;
    an asymmetric concave.

It is generally presented that achromatic lens systems, as demonstrated in FIGS. 7a3 and 7a4, are usually achieved by combination of two or more singlet lenses, said combination being designed to lessen lens "chromatic aberation", (eg. observable as varying focal length, and/or spot size at a given distance from a lens as a function of wavelength). The source of chromatic characteristics in lenses is found in dispersion by materials from which lenses are made, said dispersion being quantified as a wavelength dependent "index of refraction" which causes different wavelengths of electromagnetic radiation to be refracted differently. Generally, what is required to form achromatic lenses is a combination of two elements which each demonstrate different, (not merely offset), indicies of refraction vs. wavelength curves. When lenses are applied in ellipsometers, chromatic aberation can be detrimental to their performance because it increases spot size of a beam of electromagnetic radiation at the surface of a sample under investigation, which increased spot size is accompanied by spectroscopically varying angle-of-incidence spread, and intensity over the area of said spot. Of course, the larger the spectral range, the more pronounced become the potentially adverse affects of chromatic aberation.

It is also noted that ideal lenses do not attenuate the magnitude of $r_p$ or $r_s$ orthogonal components, (or at least do not change their ratio, $r_p/r_s$), and also do not enter phase shift between $r_p$ or $r_s$ orthogonal components when said beam of electromagnetic radiation is caused to pass therethrough. While control of the effect of a lens on a ratio, $(r_p/r_s)$, of electromagnetic beam orthogonal components can often rather successfully be accomplished by causing a beam of electromagnetic radiation to approach a surface of a lens along essential a normal to a surface thereof, this is not the case regarding phase shift entered between $r_p$ and $r_s$ orthogonal components of a said beam of electromagnetic radiation caused to pass therethrough. That is, input, and output, lenses can demonstrate "birefringence", in that the $r_p$ orthogonal component is "retarded" by a different amount than is the $r_s$ orthogonal component when said beam of electromagnetic radiation is caused to pass therethrough. To complicate matters, this "birefringent" effect also varies with wavelength and with stresses which can develop in a lens during use because of temperature and physical changes etc.

In summary, the present invention discloses that multi-element lenses can be produced that provide essentially constant focal lengths and small spot size over a large spectroscopic range of wavelengths, and that said multi-element lenses can be produced which demonstrate small birefringence.

With the just recited listing of lens construction in mind, it should be appreciated that the disclosed invention can comprise a spectroscopic ellipsometer sequentially comprising:
  a) a source of a spectroscopic beam electromagnetic radiation;
  b) a polarizer element;

in either order elements c and d:
 c) optionally a compensator element;
 d) said input lens;
 e) a material system;

in either order elements f and g:
 f) said output lens;
 g) optionally a compensator element;
 h) an analyzer element; and
 i) a detector System.

As demonstrated in Patent Nos. 5,929,995 and 5,969,818 beam directing means and/or windows can be located at least one selection from the group consisting of:
 a) between said source of a spectroscopic beam electromagnetic radiation and said material system; and
 b) between said material system and said detector system.

The disclosed invention san also be described as a system for monitoring change in:
 the intensity of; and/or
 the ratio of and/or
 the phase between orthogonal components in;

a spectroscopic beam of electromagnetic radiation which is caused by interaction with a material system;

said system comprising at least one lens which is of multiple element construction and positioned so that beam of electromagnetic radiation transmits therethrough, wherein, at least two elements thereof are made from different materials, such that in use the focal length for each wavelength in a range of wavelengths is within an acceptable range of focal lengths;
 said at least one multiple element lens being characterized by at least one selection from the group consisting of:
  a) the focal length is between forty and forty-one millimeters over a range of wavelengths of at least two-hundred to seven-hundred nanometers;
  b) the focal length varies by less than five (5%) percent over a range of wavelengths of between two-hundred and five-hundred nanometers; and
  c) the spot diameter at the focal length is less than seventy-five microns over a range of wavelengths of at least two-hundred to seven-hundred nanometers;

said system further comprising at least one compensator positioned so that beam of electromagnetic radiation transmits therethrough, said compensator being characterized by a selection from the group consisting of:
 said at least one compensator(s) produces a retardance of between seventy-five (75) and one-hundred-thirty (130) degrees over a range of wavelengths defined by a selection from the group consisting of:
  a. between one-hundred-ninety (190) and seven-hundred-fifty (750) nanometers;
  b. between two-hundred-forty-five (245) and nine-hundred (900) nanometers;
  c. between three-hundred-eighty (380) and seventeen-hundred (1700) nanometers;
  d. within a range of wavelengths defined by a maximum wavelength (MAXW) and a minimum wavelength (MINW) wherein the ratio of (MAXW)/(MINW) is at least one-and-eight-tenths (1.8); and
 said at least one compensator(s) produces a retardation between thirty (30.0) and less than one-hundred-thirty-five (135) degrees over a range of wavelengths specified from MINW to MAXW by a selection from the group consisting of:
  a. MINW less than/equal to one-hundred-ninety (190) and MAXW greater than/equal to seventeen-hundred (1700);
  b. MINW less than/equal to two-hundred-twenty (220) and MAXW greater than/equal to one-thousand (1000) nanometers;
  c. within a range of wavelengths defined by a maximum wavelength (MAXW) and a minimum wavelength (MINW) range where (MAXW)/(MINW) is at least four-and one-half (4.5).

Said at least one multiple element lens comprises at least two elements which are made from different materials independently selected from the group consisting of:
 $CaF_2$;
 $BaF_2$;
 LiF;
 $MgF_2$;
 fused silica;
 a void region;
 a gas filled region;
 a liquid filled region; and
 a functional equivalent to a void region.

During data collection, said at least one compensator can be caused to perform motion selected from the group consisting of:
 continuously rotates; and
 sequentially rotates through a plurality of discrete angles;

around an axis defined by the locus of the spectroscopic electromagnetic beam as it transmits therethrough.

Regarding the at least one multiple element lens, it typically demonstrates at least some birefringence.

As another previously disclosed, (in Co-Pending application Ser. No. 09/517,125), non-limiting example, the spectroscopic ellipsometer system can provide at least one means for discretely, sequentially, modifying a polarization state of a beam of electromagnetic radiation provided by said source of polychromatic electromagnetic radiation through a plurality of polarization states, can comprise an essentially circular "wheel" element with a plurality of discrete polarization state modifier elements mounted thereupon, on the perimeter thereof, and projecting perpendicularly to a surface of said essentially circular "wheel". The essentially circular "wheel" element further comprises a means for causing rotation about a normal to said surface thereof, such that in use said essentially circular "wheel" element is caused to rotate to position a discrete polarization state modifier element such that the beam of electromagnetic radiation, provided by said source of polychromatic electromagnetic radiation, passes therethrough.

As another previously disclosed, (in Co-Pending application Ser. No. 09/517,125), non-limiting example, the spectroscopic ellipsometer system at least one means for discretely, sequentially, modifying a polarization state of a beam of electromagnetic radiation provided by said source of polychromatic electromagnetic radiation through a plurality of polarization states, can comprise a plurality of discrete polarization state modifier elements mounted on a slider element which is mounted in a guide providing element. During use sliding the slider element to the right or left serves to position a discrete polarizer element such that said a beam of electromagnetic radiation, provided by said source of polychromatic electromagnetic radiation, passes therethrough.

Continuing, again as previously disclosed, (in application Ser. No. 09/517,125, now U.S. Pat. No. 6,268,917), it is further noted that a system for providing an output beam of polychromatic electromagnetic radiation which has a relatively broad and flattened Intensity vs. Wavelength characteristic over a wavelength spectrum for use in said present invention systems can be applied in the present invention system. The reason for doing so is to provide an output beam of polychromatic electromagnetic radiation which is substantially a comingled composite of a plurality of input beams of polychromatic electromagnetic radiation which individually do not provide as relatively broad and flattened a intensity vs. wavelength characteristic over said wavelength spectrum, as does said output comingled composite beam of polychromatic electromagnetic radiation. The system for providing an output beam of polychromatic electromagnetic radiation, which has a relatively broad and flattened intensity vs. wavelength characteristic over a wavelength spectrum, comprises:

a. at least a first and a second source of polychromatic electromagnetic radiation; and b. at least a first electromagnetic beam combining means comprising a plate, (eg. uncoated fused silica or glass etc. such that transmission characteristics thereof are determined by angle-of-incidence and polarization state of a beam of electromagnetic radiation).

The at least a first electromagnetic beam combining means is positioned with respect to said first and second sources of polychromatic electromagnetic radiation such that a beam of polychromatic electromagnetic radiation from said first source of polychromatic electromagnetic radiation passes through said at least a first electromagnetic beam combining means, and such that a beam of polychromatic electromagnetic radiation from said second source of polychromatic electromagnetic radiation reflects from said at least a first electromagnetic beam combining means and is comingled with said beam of polychromatic electromagnetic radiation from said first source of polychromatic electromagnetic radiation which passes through said at least a first electromagnetic beam combining means. The resultant beam of polychromatic electromagnetic radiation exiting the first electromagnetic beam combining means is substantially an output beam of polychromatic electromagnetic radiation which has a relatively broad and flattened intensity vs. wavelength over a wavelength spectrum, comprising said comingled composite of a plurality of input beams of polychromatic electromagnetic radiation which individually do not provide such a relatively broad and flattened intensity vs. wavelength over a wavelength spectrum characteristic. Said system for providing an output beam of polychromatic electromagnetic radiation which has a relatively broad and flattened intensity vs. wavelength characteristic over a wavelength spectrum can also be optionally further characterized by a third source of polychromatic electromagnetic radiation, and/or a second electromagnetic beam combining (BCM) means comprising an uncoated plate, (eg. fused silica or glass etc. such that transmission characteristics thereof are determined by angle-of-incidence and polarization state of a beam of electromagnetic radiation). The second electromagnetic beam combining means, when present, is positioned with respect to said comingled beam of polychromatic electromagnetic radiation which has a relatively broad and flattened intensity vs. wavelength over a wavelength spectrum and which exits said at least a first electromagnetic beam combining means, such that it passes through said second electromagnetic beam combining means. The second electromagnetic beam combining means is also positioned with respect to the third source of polychromatic electromagnetic radiation, (when present), such that a beam of electromagnetic radiation from said third source of polychromatic electromagnetic radiation reflects from said second electromagnetic beam combining means, such that a second resultant beam of polychromatic electromagnetic radiation which is substantially an output beam of polychromatic electromagnetic radiation which has a relatively even more broadened and flattened intensity vs. wavelength over a wavelength spectrum, comprising said comingled composite of a plurality of input beams of polychromatic electromagnetic radiation from said first, second and third sources, which first, second and third sources individually do not provide such a relatively even more broadened and flattened intensity vs. wavelength over a wavelength spectrum characteristic.

At least one of said first and second, (when present), electromagnetic beam combining means can be pivotally mounted such that, for instance, the angle at which a beam of polychromatic electromagnetic radiation from the second source of polychromatic electromagnetic radiation reflects from the at least one electromagnetic beam combining means can be controlled to place it coincident with the locus of a beam of polychromatic electromagnetic radiation transmitted therethrough. Pivot means providing two dimensional degrees of rotation freedom are preferred in this application. Further, where sources of polychromatic electromagnetic radiation can be moved, the pivot capability can be utilized to allow use of optimum tilts of electromagnetic beam combining means. That is, transmission and reflection characteristics of an electromagnetic beam combining means vary with the angle of incidence a transmitted or reflected beam makes with respect thereto, and pivot means can allow adjusting tilt to optimize said characteristics.

Further, as the polarizer in the present invention spectroscopic ellipsometer system remains essentially fixed in position during data acquisition, it is noted that it is preferable that a source of electromagnetic radiation, and/or a present Polarizer or Polarization State Generator be positioned or configured so as to pass predominately "S" Polarized electromagnetic radiation, as referenced to said beam combining system. The reason for this is that the split between "S" polarization transmission and reflection components is less, as a function of wavelength and electromagnetic beam angle-of-incidence to said beam combining means, when compared to that of the "P" components. The "P" component is far more affected, particularly around a Brewster angle condition, hence, where an "S" component, with reference to a beam combining system, is utilized, it is to be appreciated that variation in intensity of transmitted and reflected beams of electromagnetic radiation output from the beam combining system, as functions of wavelength and the angles of incidence of beams of electromagnetic radiation from sources of said transmitted and reflected beams of electromagnetic radiation, is minimized, as compared to variation which occurs in "P" components.

It is noted that the polarizer and analyzer thereof, which are essentially fixed in position during data acquisition, are not necessarily absolutely fixed in position. Said polarizer and analyzer are preferably what is properly termed "Rotatable". That is they can be rotated to various positions by a user between data acquisitions, but they are not caused to be Rotating while data is being acquired. (Typical positioning of analyzer and polarizer azimuthal angles are plus or minus forty-five (+/−45) degrees)).

It is also noted that operation of the present invention can be generally improved by improving the quality of the electromagnetic radiation.

A first approach is to provide a back reflector behind a source of electromagnetic radiation, which serves to direct electromagnetic radiation which exits the source in a useful direction.

Another approach is to provide a reflecting means in the pathway of the electromagnetic beam, upon which reflecting means is a coating which emphasises reflection of the UV and particularly at 193 nm. An example of such a coating on a reflective means is 600 Angstroms of Silicon Dioxide atop Silicon. This approach enables setting "gain" providing means at higher levels to emphasize UV signals, while not over amplifying, and even saturating higher intensity wavelengths signals.

Another approach is to coat transmissive elements such as lenses present in the system, to minimize entry and exit losses caused thereby, and improve overall UV transmission therethrough. An example is a single 300 Angstrom layer of $MgF_2$. Multilayer coatings can also be used.

Another approach is to provide a Grating which has characteristics that emphasize UV wavelengths and/or direct a utilized "Order" of wavelengths in a direction which is subject to less influence by the zero and/or other orders.

Further, application of baffling to block access of zero and/or other orders of electromagnetic radiation to detector means can be applied.

Approaches which focus on optical fibers are:

Another approach is to eliminate optical fibers which, while convenient for use directing electromagnetic radiation, also serve to attenuate UV wavelength intensity via entry loss and transmission attenuation.

However, if optical fibers are utilized, to reduce UV intensity at fiber entry loss a narrow slit (eg. smaller that the fiber dimension), can be placed at the entry to the fiber.

The following approaches focus on increasing the amount of UV electromagnetic radiation and can be practiced independently or in combination:

Another approach is to utilize a source of electromagnetic radiation which emphasises UV wavelength production. Various wattage lamps (eg. 35, 75 and 150 can be applied and where necessary can involve application of various indirect heat sink based cooling and produced ozone containment.

Another approach is to, in the case of rotating compensator ellipsometers, reduce the rotation speed of the compensator so that for the same number of rotations more total electromagnetic radiation passes therethrough and reaches the detector.

Another approach is to take multiple scans of data to improve signal to noise.

Another approach is to combine the output of multiple pixels in a detector which receive UV radiation.

It is also disclosed that the presently disclosed spectroscopic ellipsometer can be mounted in a Chamber for controlling the ambient. Examples of the Chamber are:

it comprises at least one chamber region in which is present polarization state generator comprising component(s) prior to said material system, said material system, and polarization state detector comprising component(s) after said material system;

it comprises at least three chamber regions, in one of which is present polarization state generator comprising component(s) prior to said material system, in the second of which is present the material system and in the third of which is present polarization state detector comprising component(s) after said material system;

it comprises at least two chamber regions, in one of which is present polarization state generator comprising component(s) prior to said material system and said material system, and in the second of which is present polarization state detector comprising component(s) after said material system;

it comprises at least two chamber regions, in one of which is present polarization state generator comprising component(s) prior to said material system, and in the second of which is present polarization state detector comprising component(s) after said material system and said material system.

It is believed that the present invention spectroscopic ellipsometer system combination comprising:

polarizer and analyzer, (which are both fixed in position during data acquisition); and at least one rotating or stepwise rotatable compensator means for discretely, sequentially, modifying a polarization state of a beam of electromagnetic radiation provided by said source of polychromatic electromagnetic radiation through a plurality of polarization states, said means being present at least one location selected from the group consisting of:
between said polarizer and said stage for supporting a sample system; and
between said stage for supporting a sample system and said analyzer; and at least one multiple element lens present at least one location selected from the group consisting of:
between said polarizer and said stage for supporting a sample system; and
between said stage for supporting a sample system and said analyzer;

said at least one rotating or stepwise rotatable compensator means for discretely, sequentially, modifying a polarization state of a beam of electromagnetic radiation provided by said source of polychromatic electromagnetic radiation through a plurality of polarization states, and said at least one multiple element lens being positioned so that said beam of electromagnetic radiation transmits therethrough in use;

is Patentably distinct over all prior art other than Patents which are co-owned by the J.A. Woollam Co. Inc. from which this Application Continues-In-Part or from which this Application otherwise has priority benefit.

The present invention will be better understood by reference to the Detailed Description Section of this Specification, in combination with the Drawings.

SUMMARY

It is therefore a primary purpose and/or objective of the present invention to disclose a combination of:

spectroscopic ellipsometer and combined spectroscopic reflectometer/ellipsometer systems, which present invention system includes, in the spectroscopic ellipsometer portion thereof, provision of polarizer and analyzer elements which are fixed in position during data acquisition procedures, and at least one continuously rotating or stepwise rotatable compensator means for imposing a plurality of sequentially discrete, rather than continuously varying, polarization states onto a beam of electromagnetic radiation caused to be present in said spectroscopic ellipsometer system; and multi-element lens systems which enables practice of focused beam small-spot spectroscopic ellipsometry over a large wavelength range, including into the deep UV, (eg. wavelengths down to and below 190 NM); (multi-element lenses which comprise elements made of different materials allow essentially the same focal length to be achieved over a wide wavelength range being preferred).

It is yet another purpose and/or objective of the presently disclosed invention to disclose a preferred, but not limiting, source of electromagnetic radiation which provides a plurality of wavelengths combined from a plurality of sources.

It is another purpose and/or objective yet of the presently disclosed invention to teach containing a spectroscopic ellipsometer in an environmental chamber.

Other purposes and/or objectives will become clear from a reading of the Specification and Claims.

BRIEF DESCRIPTION OF THE DRAWINGS

FIGS. 3j1–3p show additional functional construction of compensator systems which are within the scope of the present invention.

FIGS. 7a1 and 7a2 show comparison Focal Length and Spot Size respectively vs. Wavelength for single and multiple element lenses.

FIGS. 7a3 and 7a4 show typical single and dual multiple element lens system construction.

FIGS. 7a5–7a26 show possible multiple element lens constructions.

FIGS. 7a27–7a32 show possible three element lens constructions.

FIG. 8 demonstrates placing a spectroscopic ellipsometer in an environmental chamber.

DETAILED DESCRIPTION

Figure 1:
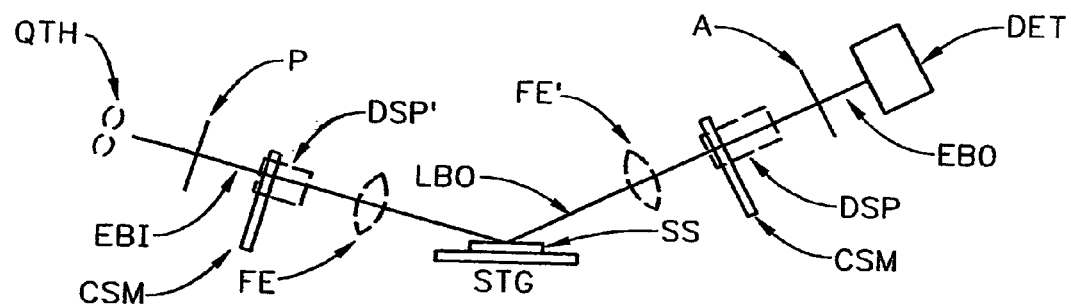
FIG. 1 shows a present invention spectroscopic ellipsometer system configuration.

FIGS. 1–6 show material previously disclosed in Co-Pending application Ser. No. 09/517,125, and FIGS. 7a1–7a26 show material previously disclosed in Co-Pending application Ser. No. 09/583,229. More specifically, it is noted that FIGS. 3e–3p show demonstrative designs for substantially achromatic Transmissive Compensators, and FIGS. 7a3–7a26 show demonstrative designs for substantially Achromatic Multiple Element Transmissive Lenses applied in the present invention in combination.

Turning now to FIG. 1, there is shown a demonstrative spectroscopic ellipsometer system configuration. Shown are a source of polychromatic electromagnetic radiation (QTH), (eg. a quartz-halogen-lamp), a polarizer (P) a stage for supporting a sample system (STG) with a sample system (SS) present thereupon, a means (DSP) for discretely, sequentially, modifying a polarization state of a beam of electromagnetic radiation provided by said source of polychromatic electromagnetic radiation through a plurality of polarization states by passage therethrough, an analyzer (A), and a detector system (DET). (Note preferred detector systems are spectroscopic, (multi-element), such as Bucket Brigade, Diode and CCD arrays and that "off-the-shelf" spectrometer systems such as manufactured by Zeiss can also be applied). Shown also are ellipsometer electromagnetic beam in (EBI) and ellipsometer electromagnetic beam out (EBO). It is noted that said means (DSP) for discretely, sequentially, modifying a polarization state of a beam of electromagnetic radiation, while shown as present between said stage (STG) for supporting a sample system (SS) and said analyzer (A), can generally be present as (DSP') between said polarizer (P) and said stage (STG) for supporting a sample system (SS), and/or as (DSP) between said stage (STG) for supporting a sample system and said analyzer (A).

It is noted that the combination of elements (QTH), (P), and (DSP') is sometimes described as a Polarization State Generation System, and the combination of elements (DSP) (A) and (DET) is sometimes described as a Polarization State Detection System. Also, it is to be understood that the Polarization State Detection System could be rotated so as to position the Detector (DET) to detect electromagnetic radiation transmitted through the Sample (SS), and remain within the scope of the invention.

Figure 2:
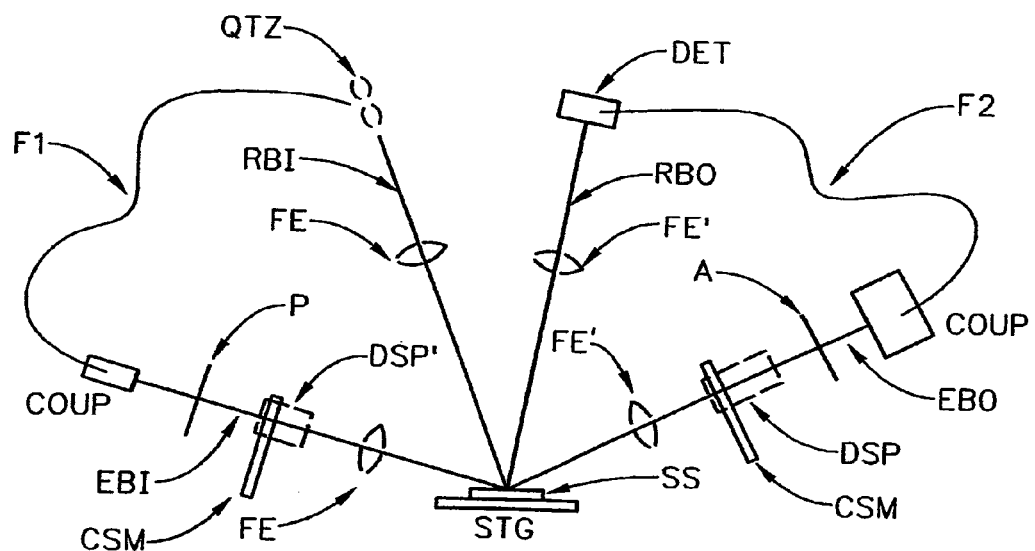
FIG. 2 shows a combined present invention spectroscopic reflectometer/ellipsometer system.

FIG. 2 shows a combined spectroscopic reflectometer/ellipsometer system wherein the source of polychromatic electromagnetic radiation (QTH), and detector (DET) system are common to both, and wherein the spectroscopic ellipsometer system is shown as being provided input and output electromagnetic beam access via fiber optics (F1) and (F2). Shown are near-normal orientation reflectometer electromagnetic beam in (RBI) and reflectometer electromagnetic beam out (RBO), as well as sample system (SS) specific near Brewster condition ellipsometer electromagnetic beam in (EBI) and ellipsometer electromagnetic beam out (EBO). While not shown, it is noted that the source of polychromatic electromagnetic radiation (QTH), and detector (DET) system can be located distal from both the reflectometer and ellipsometer portions of the combined spectroscopic reflectometer/ellipsometer system, with fiber optics being present to interface to the reflectometer portion as well.

Figure 3A:
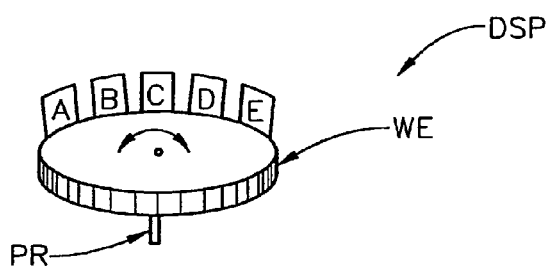
FIG. 3a shows a frontal perspective view of a discrete state polarizer comprising a wheel with five discrete polarizer elements mounted thereupon.
Figure 3B:
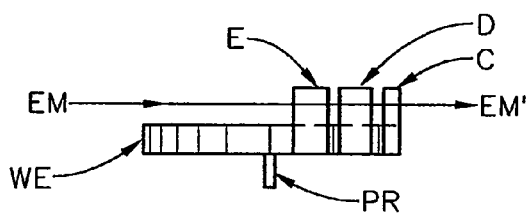
FIG. 3b shows a side elevational view of a discrete state polarizer, as in FIG. 3a, oriented so that an electromagnetic beam passing through one of the discrete polarizer five elements.
Figure 3C:
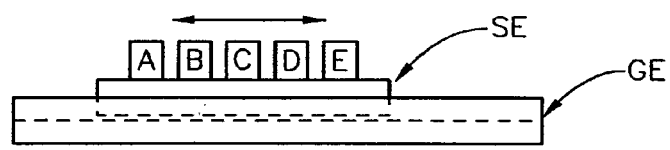
FIG. 3c shows a front elevational view of a discrete state polarizer with five laterally slideably mounted discrete polarizer elements mounted therein.

In both FIGS. 1 and 2, there can optionally be other (eg. focusing elements ((FE) (FE')), present on one or both sides of the sample system (SS), as shown in dashed lines. Said other elements appear ellipsometrically indistinguishable with polarization state modifiers during use. Also shown in FIGS. 1 & 2 are Compensator Rotating or Stepping Means (CSM) (CSM') for use in continuously rotating or stepwise rotating compensator (DSP) and/or (DSP') or operating means as shown in FIGS. 3a–3c. The presently disclosed invention provides that at least one focusing element ((FE) (FE')) will be present and be of multiple element construction, as discussed in conjunction with FIGS. 7a3–7a26.

FIG. 3a shows a frontal perspective view of a discrete state polarizer (DSP) comprising an essentially circular "wheel" element (WE) with five discrete polarization state modifiers elements (A) (B) (C) (D) and (E) mounted thereupon on the perimeter thereof, such that said and projecting discrete polarization state modifier elements (A) (B) (C) (D) and (E) project perpendicularly to a surface thereof. FIG. 3b shows a side elevational view of a discrete state polarizer, as in FIG. 3a, oriented so that an electromagnetic beam (EM) passing through one (C) of the five discrete polarization state modifiers (A) (B) (C) (D) and (E) elements. Note that discrete polarizer elements (A) and (B) are located behind discrete polarizer elements (E) and (D) respectively. Also note that if the essentially circular "wheel" element (WE) is caused to rotate about the pivot rod (PR) which projects from a lower surface of said essentially circular "wheel" element, each of the various five discrete polarizer (A) (B) (C) (D) and (E) elements can be rotated into the position in which is shown discrete polarizer element (C). FIG. 3c shows a front elevational view of a discrete state polarizer with five laterally slideably mounted discrete polarizer (A) (B) (C) (D) and (E) elements mounted on a slider element (SE) which is mounted in a guide providing element (GE) therein. Sliding the slider element (SE) to the right or left serves to position each of the five discrete polarizer (A) (B) (C) (D) and (E) elements in a position at which an electromagnetic beam of radiation can be caused to be present. (Note more or less than five discrete polarizer elements can be present).

Figure 3D:
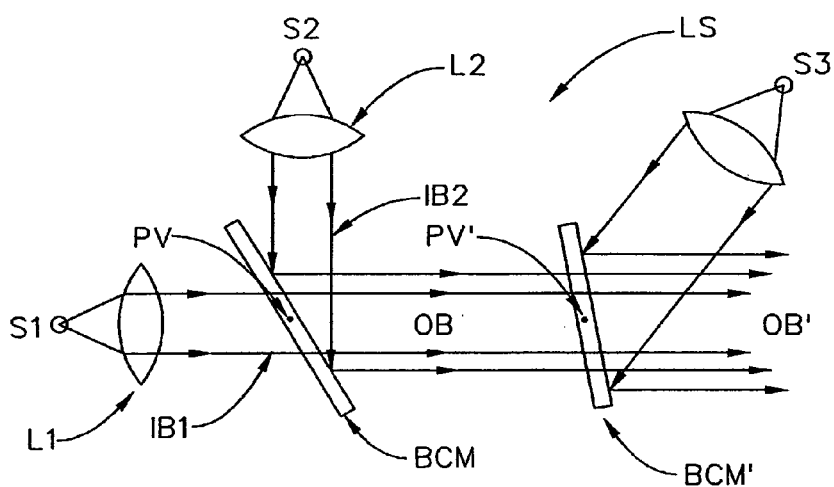
FIG. 3d shows a present invention system for providing an output beam (OB) or (OB') of polychromatic electromagnetic radiation which has a relatively broad and flattened intensity vs. wavelength characteristic over a wavelength spectrum.
Figure 4:
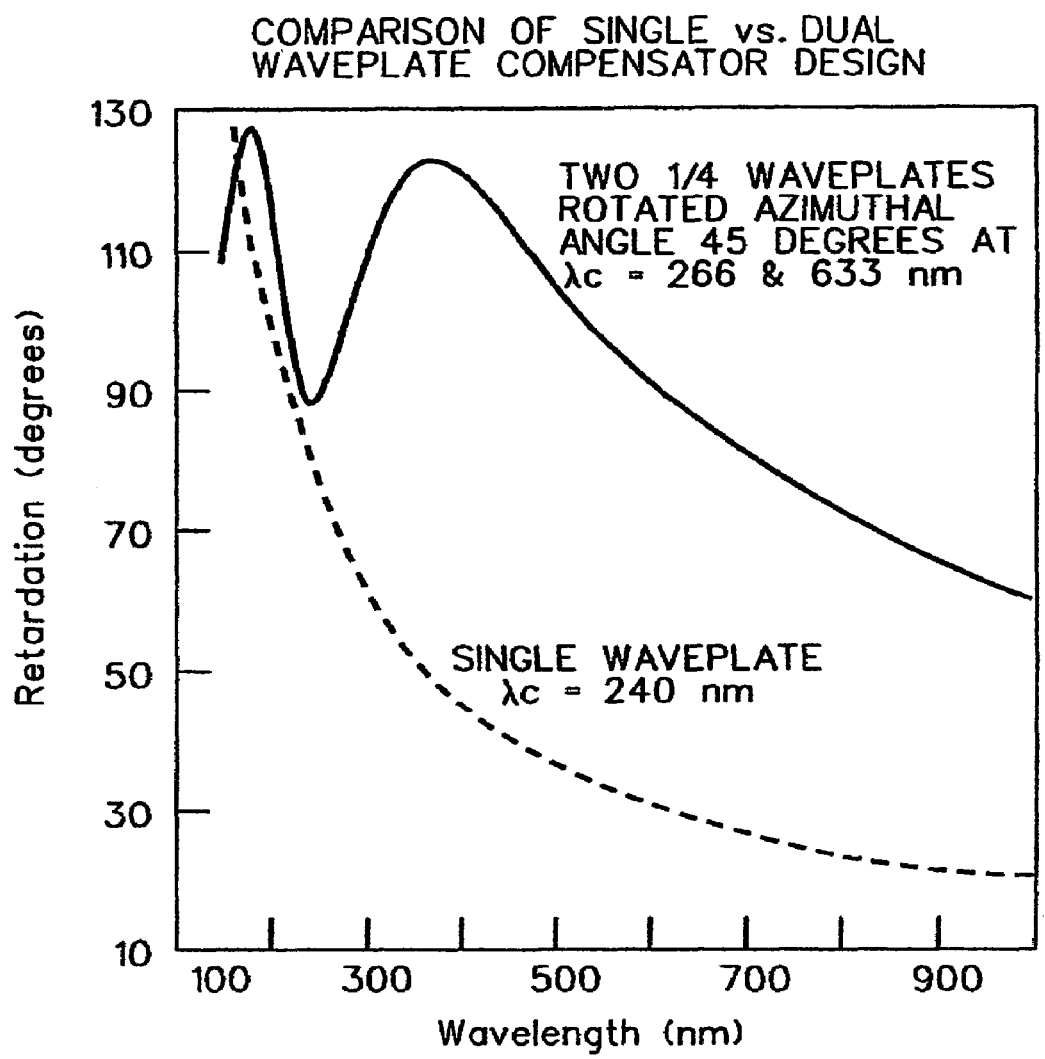
FIGS. 4–6 provide insight to the Psuedo-Achromatic characteristics achieved by a FIG. 3f Compensator design.
Figure 5:
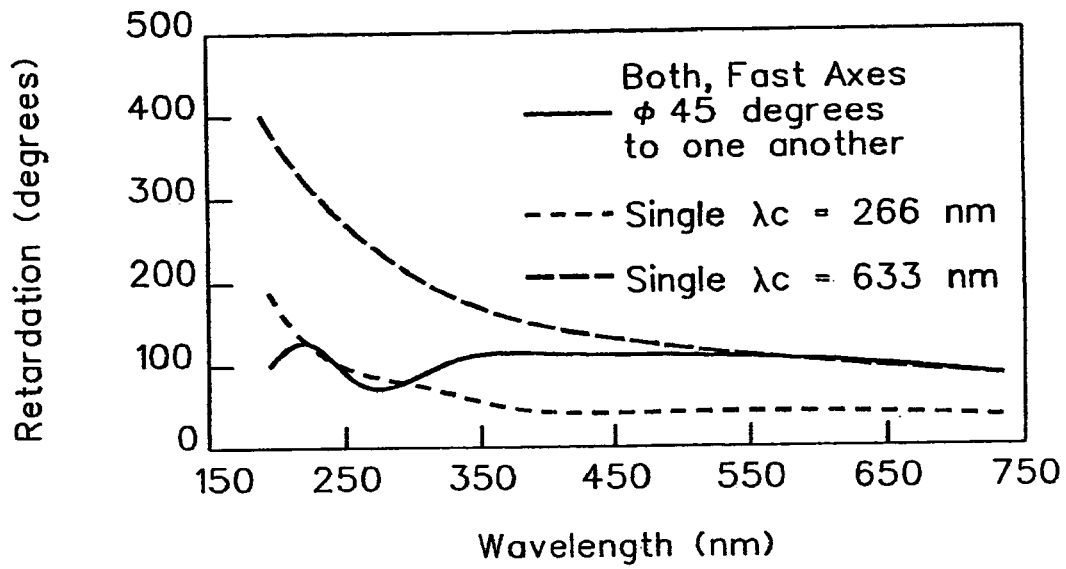
Figure 6:
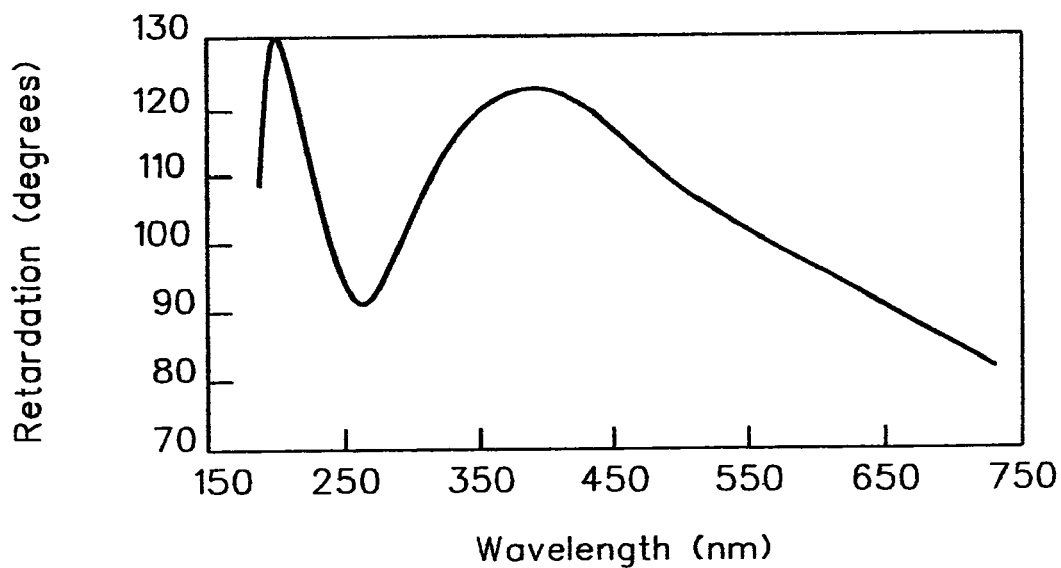

The embodiments in FIGS. 3a–3c have been found to be difficult to practice, however, and it has been determined that a better approach is to utilize transmissive rotatable compensator means to provide the discrete polarization state changes. FIGS. 3e, 3f, 3g, 3h and 3i demonstrate that at least one Compensator can be applied as (DSP) or (DSP') in FIGS. 1 and 2, which at least one Compensator (DSP) and/or (DSP'), is, in use, rotated about the locus of the electromagnetic beam (EBI) or (EBO), by Compensator Rotation Stepping Means (CSM') and/or (CSM). That is, the presently disclosed invention then comprises a Discrete Polarization State Spectroscopic Ellipsometer System, with the clarification being that the Discrete Polarization State effecting means (DSP) and/or (DSP') is preferably a Rotatable Compensator, which during use is continuously rotated or stepped through a plurality of discrete rotation angles, and then held motionless during data acquisition. While not limiting, a utility providing specific embodiment applies Psuedo-Achromatic Rotatable Compensators. (Note, FIGS. 4–6 show various Psuedo-Achromatic Retardation vs. Wavelength characteristics possible utilizing multiple element compensators, as shown in FIG. 3f).

Further, essentially any Compensator which can be placed into a beam of electromagnetic radiation can be applied, such as those disclosed in claim 9 of U.S. Pat. No. 5,872, 630, (which 630 Patent is incorporated by reference hereinto):

Berek-type;
In-Plane Non-Berek-type;
Zero Order;
Zero Order comprising a plurality of plates;
Rhomb;
Polymer;
Achromatic Crystal; and
Psuedo-Achromatic.

Figure 3E:
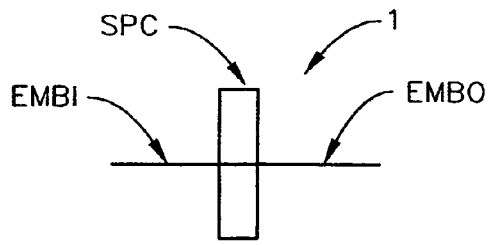
FIGS. 3e–3i demonstrate functional construction of preferred present invention compensator systems.
Figure 3F:
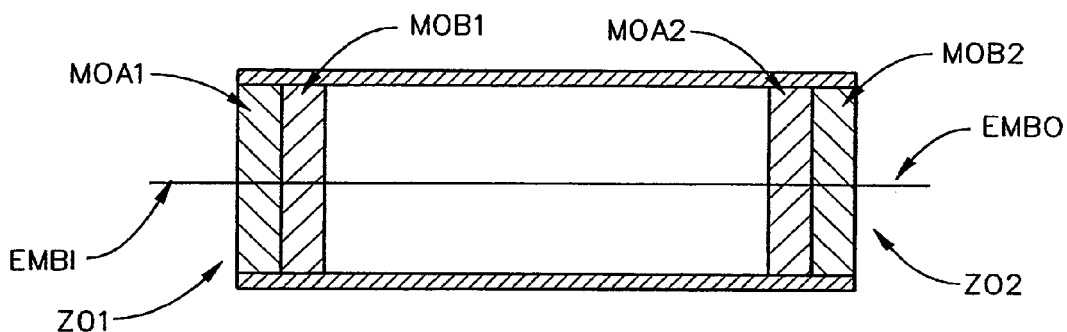
Figure 3G:
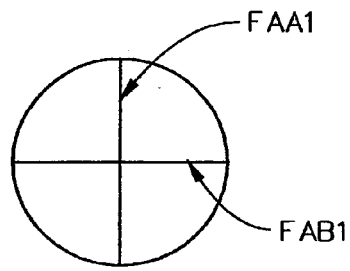
Figure 3H:
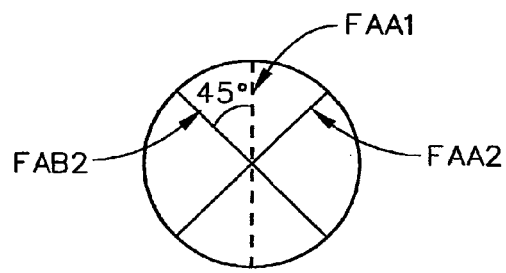
Figure 3I:
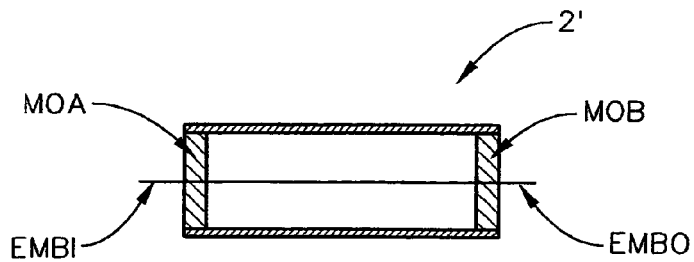
Figure 3L:
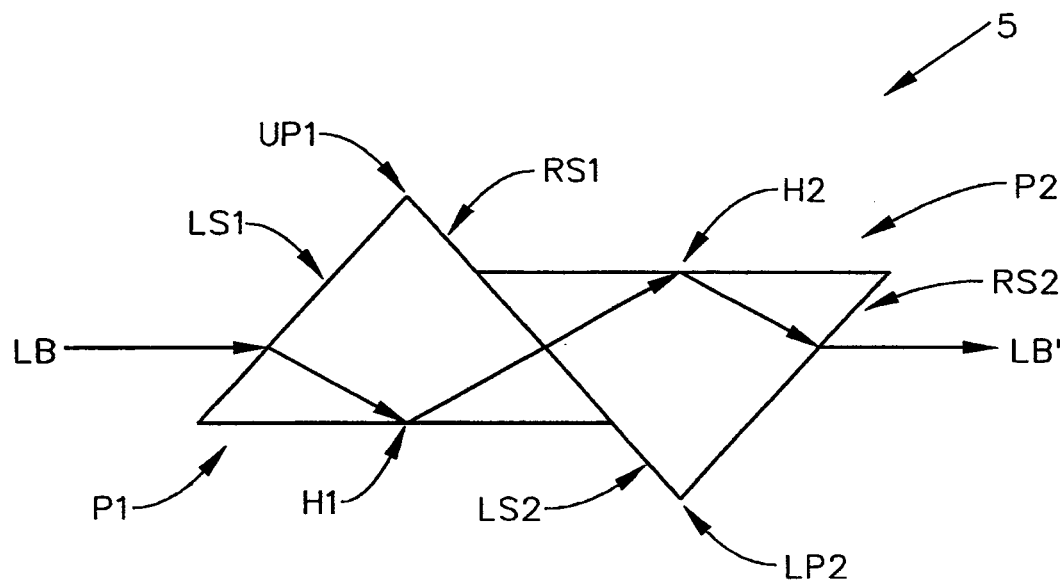

FIGS. 3e, 3f, 3g, 3h and 3i demonstrate functional construction of preferred present invention compensator systems. FIG. 3e simply exemplifies that a single plate (SPC) compensator (1) can be applied. FIG. 3f demonstrates construction of a compensator (2) from first (ZO1) and second (ZO2) effectively Zero-Order, (eg. Quartz or Bicrystaline Cadnium Sulfide or Bicrystaline Cadnium Selenide), Waveplates, each of which effective Zero-Order Waveplates (ZO1) & (ZO2) is shown to be constructed from two Multiple Order waveplates, (ie. (MOA1) & (MOB1) and (MOA2) & (MOB2), respectively). The fast axes (FAA2) & (FAB2) of said second effective Zero-Order Waveplate (ZO2) are oriented away from zero or ninety degrees, (eg. in a range around a nominal forty-five degrees such as between forty and fifty degrees), with respect to the fast axes (FAA1) & (FAB1) of said first effective Zero-Order Waveplate (ZO1). In particular FIG. 14b is a cross-sectional side view of a present invention preferred compensator (PC) constructed from a first effective zero-order plate (ZO1) which is constructed from two multiple order plates (MOA1) and (MOB1), and a second effective zero-order plate (ZO2) which is constructed from two multiple order plates (MOA2) and (MOB2). An entered electromagnetic beam (EMBI) emerges as electromagnetic beam (EMBO) with a retardation entered between orthogonal components thereof with a Retardation vs. Wavelength. FIGS. 3g and 3h are views looking into the left and right ends of the preferred present invention Compensator (PC) as shown in FIG. 3f, and show that the Fast Axes (FAA2) and (FAB2) of the second effective Zero-Order Waveplate (ZO2) are rotated away from zero or ninety degrees and are ideally oriented at forty-five degrees, with respect to the Fast Axes (FAA1) & (FAB1) of the first effective Zero-Order Waveplate (ZO1). (Note that the fast axis (FAA1) of the first effective Zero-Order Waveplate (ZO1) is shown as a dashed line in FIG. 3h, for reference). FIG. 3i demonstrates functional construction of another preferred compensator (2') which is constructed from two per se. single plate Zero-Order Waveplates (MOA) and (MOB), which are typically made of materials such as mica or polymer.

(It is specifically to be understood that a present invention compensator system can be comprised of at least one Zero-Order waveplate and at least one effectively Zero-Order waveplate in combination, as well as combinations comprised of two actual Zero-Order waveplates or two effectively Zero-Order waveplates).

FIGS. 3j1–3p demonstrate additional compensators which can be applied in the present invention.

FIG. 3j1 shows that the first additional present invention retarder system (3) comprises a first triangular shaped element (P1), which as viewed in side elevation presents with first (OS1) and second (OS2) sides which project to the left and right and downward from an upper point (UPI). Said first triangular shaped element (P1) first (OS1) and second (OS2) sides have reflective outer surfaces. Said retarder system (3) further comprises a second triangular shaped element (P2) which as viewed in side elevation presents with first (IS1) and second (IS2) sides which project to the left and right and downward from an upper point (UP2), said second triangular shaped element (P2) being made of material which provides internally reflective, phase delay introducing, interfaces on first (IS1) and second (IS2) sides inside thereof. Said second triangular shaped element (P2) is oriented with respect to the first triangular shaped element (P1) such that the upper point (UP2) of said second triangular shaped element (P2) is oriented essentially vertically directly above the upper point (UP1) of said first triangular shaped element (P1). In use an input electromagnetic beam of radiation (LB) caused to approach said first (OS1) side of said first triangular shaped element (P1) along an essentially horizontally oriented locus, is shown as being caused to externally reflect from an outer surface thereof and travel along as electromagnetic beam of radiation (R1) which is essentially upwardly vertically oriented. Next said electromagnetic beam of radiation (R1) is caused to enter said second triangular shaped element (P2) and essentially totally internally reflect from said first (IS1) side thereof, then proceed along an essentially horizontal locus and essentially totally internally reflect from the second (IS2) side thereof and proceed along an essentially downward vertically oriented electromagnetic beam of radiation (R3). This is followed by an external reflection from an outer surface of said second side (OS2) of said first triangular shaped element (P1) such that said electromagnetic beam (LB') of radiation proceeds along an essentially horizontally oriented locus, undeviated and undisplaced from the essentially horizontally oriented locus of said input beam (LB) of essentially horizontally oriented electromagnetic radiation. This is the case even when said retarder system (3) is caused to rotate. The result of said described retarder system (3) application being that retardation is entered between orthogonal components of said input electromagnetic beam of radiation (LB). Further, said first (P1) and second (P2) triangular shaped elements are typically right triangles in side elevation as shown in FIG. 3j1, and the outer surfaces of first (OS1) and second (OS2) sides are typically, but not necessarily, made reflective by the presence of a coating of metal thereupon. A coating of metal serves assure a high reflectance and good electromagnetic beam radiation intensity throughput. Also, assuming accurately manufactured right angle first (P1) and second (P2) triangular shaped elements are utilized, this compensator design provides inherent compensation of both angular and translational misalignments of the input light beam (LB). As well, the total retardence provided is compensated for angular misalignments of the input electromagnetic radiation beam. That is, if the input electromagnetic radiation beam (LB) is not aligned so as to form an angle of incidence of forty-five (45) degrees with the first outer surface (OS1), the reflected electromagnetic beam (R1) will internally reflect at the first internal surface (IS1) of the second triangular shaped element (P2) at a larger (smaller) angle than would be the case if said angle of incidence were forty-five (45) degrees. This effect, however, is directly compensated by a smaller (larger) angle of incidence of electromagnetic beam (R2) where it internally reflects from inner surface (IS2) of the second triangular shaped element (P2). As another comment it is to be understood that because of the oblique angles of incidence of the reflections from the outer surfaces (OS1) and (OS2) of the first triangular shaped element (P1) a polarimeter/ellipsometer in which said compensator (3) is present will require calibration to characterize the PSI-like component thereof.

FIG. 3j2 shows a variation (3') on FIG. 3j1, wherein the first triangular shaped element is replaced by two rotatable reflecting means, identified as (OS1') and (OS2'). This modification allows user adjustment so that the locus of an entering electromagnetic beam (LB') exits undeviated and undisplaced from an entering electromagnetic beam (LB).

FIG. 3k shows that the second additional present invention retarder system (4) comprises a parallelogram shaped element which, as viewed in side elevation, has top (TS) and bottom sides (BS), each of length (d) parallel to one another, both said top (TS) and bottom (NS) sides being oriented essentially horizontally. Said retarder system (4) also has right (RS) and left (LS) sides parallel to one another, both said right (RS) and left (LS) sides being of length (d/cos(α), where alpha (α) is shown as an angle at which said right (RS) and left (LS) sides project from horizontal. Said retarder system (4) is made of a material with an index of refraction greater than that of a surrounding ambient. In use an input beam of electromagnetic radiation (LB) caused to enter the left side (LS) of said retarder system (4), along an essentially horizontally oriented locus, is caused to diffracted inside said retarder system (4) and follow a locus which causes it to essentially totally internally reflect from internal interfaces of both said top (TS) and bottom (BS) sides, and emerge from said retarder system (4) as (LB') from the right side (RS) thereof, along an essentially horizontally oriented locus which is undeviated and undisplaced from the essentially horizontally oriented locus of said input beam (LB) of essentially horizontally oriented electromagnetic radiation. This is the case even when said retarder system (4) is caused to rotate. The result of said described retarder system (4) application being that retardation is entered between orthogonal components of said input electromagnetic beam of radiation at said internal reflections from the top (TS) and bottom (BS) surfaces. This retarder system is very robust as it is made of single piece construction. It is noted that adjustment of the angle alpha (α) in manufacture allows setting the amount of retardation which is provided by the retarder system (4). In addition, coatings can be externally applied to top (TS) and bottom surface (BS) to adjust retardation effected by internal reflection from said top (TS) and bottom (BS) surfaces. A formula which defines the retardation provided thereby being:

$$\frac{d}{h} = 2 - \tan(\phi), \text{ where } \phi = \alpha + \sin^{-1}\left(\frac{\sin(90 - \alpha)}{n}\right)$$

FIG. 31 shows that the third additional present invention retarder system (5) comprises first (P1) and second (P2) triangular shaped elements. Said first (P1) triangular shaped element, as viewed in side elevation, presents with first (LS1) and second (RS1) sides which project to the left and right and downward from an upper point (UP1), said first triangular shaped element (P1) further comprising a third side (H1) which is oriented essentially horizontally and which is continuous with, and present below said first (LS1) and second (RS1) sides. Said second triangular shaped element (P2), as viewed in side elevation, presents with first (LS2) and second (RS2) sides which project to the left and right and upward from a lower point (LP2), said second triangular shaped element (P2) further comprising a third side (H2) which is oriented essentially horizontally and which is continuous with, and present above said first (LS2) and second (RS2) sides. Said first (P1) and second (P2) triangular shaped elements being positioned so that a rightmost side (RS1) of said first (P1) triangular shaped element is in contact with a leftmost side (LS2) of said second (P2) triangular shaped element over at least a portion of the lengths thereof. Said first (P1) and second (P2) triangular shaped elements are each made of material with an index of refraction greater than that of a surrounding ambient. In use an input beam (LB) of electromagnetic radiation caused to enter the left (LS1) side of said first (P1) triangular shaped element and is caused to diffracted inside said retarder system (5) and follow a locus which causes it to essentially totally internally reflect from internal interfaces of said third sides (H1) and (H2) of said first (P1) and second (P2) triangular shaped elements, respectively, and emerge from said right side (RS2) of said second (P2) triangular shaped element as electromagnetic radiation beam (LB') which is oriented along an essentially horizontal locus which is undeviated and undisplaced from the essentially horizontally oriented locus of said input beam (LB) of essentially horizontally oriented electromagnetic radiation. This is the case even when said retarder system (5) is caused to rotate. The result of said described retarder system (5) application being that retardation is entered between orthogonal components of said input electromagnetic beam of radiation (LB). It is noted that as long as the third sides (H1) and (H2) of said first (P1) and second (P2) triangular shaped elements are parallel, the output electromagnetic beam (LB') is undeviated and undisplaced from the input electromagnetic beam (LB) in use. It is noted that The triangular shape elements (P1) and/or (P2) can be made of various materials with various indicies of refraction, and coating(s) can be applied to one or both of the third sides (H1) and (H2) of said first (P1) and second (P2) triangular shaped elements to adjust retardation entered to an electromagnetic beam (LB1).

Figure 3M:
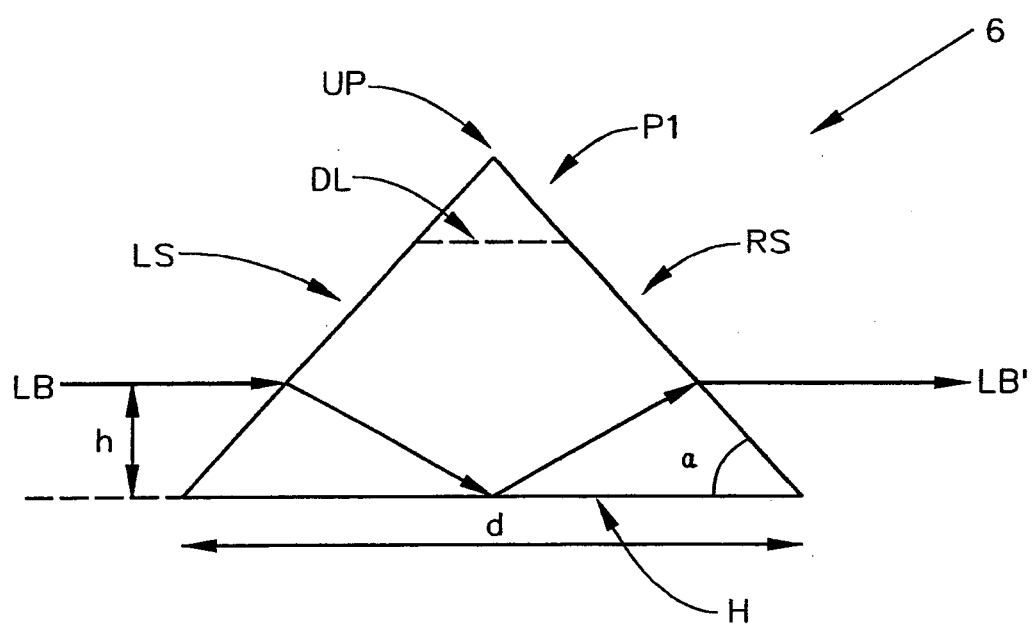

FIG. 3m shows that the forth additional present invention retarder system (6) comprises a triangular shaped element, which as viewed in side elevation presents with first (LS) and second (RS) sides which project to the left and right and downward from an upper point (UP). Said retarder system (6) further comprises a third side (H) which is oriented essentially horizontally and which is continuous with, and present below said first (LS)— and second (RS) sides. Said retarder system (6) is made of a material with an index of refraction greater than that of a surrounding ambient. In use an input beam of electromagnetic radiation (LB) caused to enter the first (LS) side of said retarder system (6) along an essentially horizontally oriented locus, is caused to diffracted inside said retarder system (6) and follow a locus which causes it to essentially totally internally reflect from internal interface of said third (H) side, and emerge from said retarder system (6) from the second (RS) side along an essentially horizontally oriented locus which is undeviated and undisplaced from the essentially horizontally oriented locus of said input beam of essentially horizontally oriented electromagnetic radiation (LB). This is the case even when said retarder system (6) is caused to rotate. The result of said described retarder system (6) application being that retardation is entered between orthogonal components of said input electromagnetic beam of radiation (LB). The FIG. 3m retarder system (6) is typically an isosceles prism which is available off-the-shelf with an angle alpha (α) of forty-five (45) degrees. As long as the input electromagnetic beam (LB) height (h) is chosen in accordance with the formula:

$$d = 2h\left(\frac{1}{\tan(\alpha)} + \tan(\phi)\right), \text{ where } \phi = \alpha + \sin^{-1}\left(\frac{\sin(90-\alpha)}{n}\right)$$

in conjunction with the index of refraction (n) of the material from which the retarder system (6) is made, and the locus of the input electromagnetic radiation beam (LB) is parallel with the third side (H) of said retarder system (6), the output electromagnetic beam (LB') will not be deviated or translated with respect to the input electromagnetic beam (LB). As well, note the dashed line (DL) below the upper point (UP). This indicates that as the region above said dashed line (DL) is not utilized, the portion of said retarder system (6) thereabove can be removed. It is also noted that the input electromagnetic beam (LB) enters and exits the retarder system (6) other than along a normal to a surface thereof, said retarder system is not an ideal retarder with a PSI of forty-five (45) degrees. It is noted that the third side (H) of the retarder system (6) can be coated to change the retardation effects of an internal reflection of an electromagnetic beam of radiation therefrom, and such a coating can have an adverse effect on the nonideal PSI characteristics.

FIG. 3p shows that the fifth additional present invention retarder system (7) comprises first (PA1) and second (PA2) parallelogram shaped elements which, as viewed in side elevation, each have top (TS1)/(TS2) and bottom (BS1)/(BS2) sides parallel to one another, both said top (TS1) (TS2) and bottom (BS1) (BS2) sides each being oriented at an angle to horizontal. Said first (PA1) and second (PA2) parallelogram shaped elements also each have right (RS1)/(RS2) and left (LS1)/(LS2) sides parallel to one another, all said right (RS1) (RS2) and left (LS1) (LS2) sides being oriented essentially vertically. Said first (PA1) and second (PA2) parallelogram shaped elements are made of material with an index of refraction greater than that of a surrounding ambient. A right most vertically oriented side (RS1) of said first parallelogram is in contact with a leftmost (LS2) vertically oriented side of the second parallelogram shaped element (PA2). In use an input beam of electromagnetic radiation (LB) caused to enter an essentially vertically oriented left side (LS1) of said first parallelogram shaped element (PA1) along an essentially horizontally oriented locus, is caused to be diffracted inside said retarder system and follow a locus which causes it to essentially totally internally reflect from internal interfaces of both said top (TS1) (TS2) and bottom (BS1) (BS2) sides of both said first and second parallelogram shaped elements (PA1) (PA2), then emerge from a right side (RS2) of said second parallelogram shaped element (PA2) along an essentially horizontally oriented locus as output beam of electromagnetic radiation (LB') which is undeviated and undisplaced from the essentially horizontally oriented locus of said input beam of essentially horizontally oriented electromagnetic radiation (LB). This is the case even when said retarder system (7) is caused to rotate. The result of said described retarder system (7) application being that retardation is entered between orthogonal components of said input electromagnetic beam of radiation (LB).

FIG. 3n1 shows that the sixth additional present invention retarder system (8) comprises first (BK1) and second (BK2) Berek-type retarders which each have an optical axes essentially perpendicular to a surface thereof. As shown by FIG. 3n2, each of said first (BK1) and second (BK2) Berek-type retarders can have fast axis which are oriented other than parallel to one another, but for the presently described retarder system it is assumed that the fast axes are aligned, (ie. an angle PHI (φ) of zero (0.0) degrees exists between fast axes of the two Berek-type (BK1) and (BK2) plates in FIG. 3n1. Said first and second Berek-type retarders each present with first and second essentially parallel sides. Said first (BK1) and second (BK2) Berek-type retarders are oriented, as viewed in side elevation, with first (LS1) and second (RS1) sides of one Berek-type retarder (BK1) being oriented other than parallel to first (LS2) and second (RS2) sides of the other Berek-type retarder (BK2). In use an incident beam of electromagnetic radiation (LB) is caused to impinge upon one of said first (BK1) Berek-type retarder on one side (LS1) thereof, partially transmit therethrough then impinge upon the second Berek-type retarder (BK2), on one side thereof (LS2), and partially transmit therethrough such that a polarized beam of electromagnetic radiation (LB') passing through both of said first (BK1) and second (BK2) Berek-type retarders emerges from the second thereof in a polarized state with a phase angle between orthogonal components therein which is different than that in the incident beam of electromagnetic radiation (LB), and in a direction which is an essentially undeviated and undisplaced from the incident beam of electromagnetic radiation. This is the case even when said retarder system (8) is caused to rotate. The result of said described retarder system (8) application being that retardation is entered between orthogonal components of said input electromagnetic beam of radiation. For insight it is mentioned that, in general, a Berek-type retarder is a uniaxial anisotropic plate with its optical axis essentially perpendicular to a surface thereof. The retardence introduced to an electromagnetic beam caused to transmit therethrough is determined by a tipping of said plate. The retardation system (8) having two such Berek-type retarders present, is, it is noted, insensitive to small angular deviations in an input electromagnetic beam as each plate contributes approximately hal of achieved retardence. This insensitivity results because if the input electromagnetic beam is slightly changed, one of said plates will contribute slightly more (less), but the second slightly less (more) retardence because of offsetting effective plate "tilts" with respect to electromagnetic beams input thereto. Also, said retarder system (8) is very nearly ideal in that the PSI component of the retarder system (8) is very near a constant forty-five (45) degrees. One problem however, is that Berek-type retarder plates exhibit a (1/wavelength) retardence characteristic which, without more, makes use over a wide spectral range difficult.

A variation of the just described retarder system (8) applies to the seventh additional present invention retarder system (9) as well, with the difference being that a FIG. 3n2 offset angle PHI (φ) other than zero (0.0) is present between fast axes of the two Berek-type plates. The description of the system remains otherwise unchanged. The benefit derived, however, is that a flatter than (1/wavelength) retardation characteristic can be achieved thereby.

FIG. 3o1 serves as the pictorial reference for the eighth additional present invention retarder system (10) which comprises first (BK1), second (BK2), third (BK3) and forth (BK4) Berek-type retarders which each have an optical axes essentially perpendicular to a surface thereof, each of which first (BK1) and second (BK2) Berek-type retarders has a fast axis, said fast axes in said first (BK1) and second (BK2) Berek-type retarders being oriented essentially parallel to one another. This is exemplified by FIG. 3o2. Said first (BK1) Berek-type retarder presents with first (LS1) and second (RS1) essentially parallel sides and said second (BK2) Berek-type retarders each present with first (LS2) and second (RS2) essentially parallel sides, and said first (BK1) and second (BK2) Berek-type retarders are oriented, as viewed in side elevation, with first (LS1) and second (RS1) sides of said first Berek-type retarder being oriented other than parallel to first (LS2) and second (RS2) sides of said second (BK2) Berek-type retarder. In use an incident beam of electromagnetic radiation (LB) is caused to impinge upon said first (BK1) Berek-type retarder on said first side (LS1) thereof, partially transmit therethrough then impinge upon the second (BK2) Berek-type retarder, on said first (LS2) side thereof, and partially transmit therethrough such that a polarized beam of electromagnetic radiation (LB') passing through both of said first (BK1) and second (BK2) Berek-type retarders emerges from the second thereof in a polarized state with a phase angle between orthogonal components therein which is different than that in the incident beam of electromagnetic radiation (LB), and in a direction which is an essentially undeviated and undisplaced from the incident beam of electromagnetic radiation (LB). Each of which third (BK3) and forth (BK4) Berek-type retarders also has a fast axis, and said fast axes in said third (BK3) and forth (BK4) Berek-type retarders are oriented essentially parallel to one another but other than parallel to the parallel fast axes of said first (BK1) and second (BK2) Berek-type retarders. Said third (BK3) Berek-type retarder presents with first (LS3) and second (RS3) essentially parallel sides, and said forth (BK4) Berek-type presents with first (LS4) and second (RS4) essentially parallel sides, and said first third (BK3) and forth (BK4) Berek-type retarders are oriented, as viewed in side elevation, with first (LS3) and second (RS3) sides of one of said third (BK3) Berek-type retarder being oriented other than parallel to first (LS4) and second (RS4) sides of said forth (BK4) Berek-type retarder; such that in use an incident beam of electromagnetic radiation (LB') exiting said second (BK2) Berek-type retarder is caused to impinge upon said third (BK3) Berek-type retarder on said first (LS3) side thereof, partially transmit therethrough then impinge upon said forth (BK4) Berek-type retarder on said first (LS4) side thereof, and partially transmit therethrough such that a polarized beam of electromagnetic radiation (LB") passing through said first (BK1), second (BK2), third (BK3) and forth (BK4) Berek-type retarders emerges from the forth (BK4) thereof in a polarized state with a phase angle between orthogonal components therein which is different than that in the incident beam of electromagnetic radiation (LB) caused to impinge upon the first (LS1) side of said first (BK1) Berek-type retarder, in a direction which is an essentially undeviated and undisplaced from said incident beam of electromagnetic radiation (LB). This is the case even when said retarder system (8) is caused to rotate. The result of said described retarder system (8) application being that retardation is entered between orthogonal components of said input electromagnetic beam of radiation.

A ninth additional present invention retarder system (11) is also pictorially represented by FIG. 3o1 and is similar to that just described excepting that the Berek-type retarder plates (BK1) and (BK2) fast axes need not be parallel to one another and the Berek-type retarder plates (BK3) and (BK4) need not be parallel to one another. However, if as a group Berek-type retarder plates ((BK1) and (BK2))/((BK3) and (BK4)) are parallel, they can be, but need not be parallel the fast axes of Berek-type retarder plates ((BK3) and (BK4))/((BK1) and (BK2)). This embodiment includes the case where all the fast axes of all Berek-type retarders (BK1), (BK2), (BK3) and (BK4) are all different.

Turning now to FIG. 3d, it is shown that the present invention system source of polychromatic radiation (QTH) as in FIG. 1, can, but not necessarily, be a system for providing an output beam (OB) of polychromatic electromagnetic radiation which has a relatively broad and flattened intensity vs. wavelength characteristic over a wavelength spectrum (generally identified as (LS)), said output beam (OB) of polychromatic electromagnetic radiation substantially being a comingled composite of a plurality of input beams, ((IB1) and (IB2)), of polychromatic electromagnetic radiation which individually do not provide as relatively broad and flattened a intensity vs. wavelength characteristic over said wavelength spectrum, as does said output comingled composite beam of polychromatic electromagnetic radiation, said system for providing an output beam of polychromatic electromagnetic radiation which has a relatively broad and flattened intensity vs. wavelength characteristic over a wavelength spectrum comprising:

a. at least a first (S1) and a second (S2) source of polychromatic electromagnetic radiation, ((IB1) and (IB2) respectively); and b. at least one electromagnetic beam combining (BCM) means comprising an uncoated plate, (eg. uncoated fused silica or glass etc. such that transmission characteristics thereof are determined by angle-of-incidence and polarization state of a beam of electromagnetic radiation).

The at least one electromagnetic beam combining means (BCM) is positioned with respect to said first (S1) and second (S2) sources of polychromatic electromagnetic radiation, ((IB1) and (IB2) respectively), such that a beam of polychromatic electromagnetic radiation (IB1) from said first (S1) source of polychromatic electromagnetic radiation passes through said at least one electromagnetic beam combining means (BCM), and such that a beam of polychromatic electromagnetic radiation (IB2) from said second (S2) source of polychromatic electromagnetic radiation reflects from said at least one electromagnetic beam combining means (BCM) and is comingled with said beam of polychromatic electromagnetic radiation (IB1) from said first source (S1) of polychromatic electromagnetic radiation which passes through said at least one electromagnetic beam combining means (BCM). The resultant beam of polychromatic electromagnetic radiation (OB) is substantially an output beam of polychromatic electromagnetic radiation which has a relatively broad and flattened intensity vs. wavelength over a wavelength spectrum, comprising said comingled composite of a plurality of input beams of polychromatic electromagnetic radiation which individually do not provide such a relatively broad and flattened intensity vs. wavelength over a wavelength spectrum characteristic. Also shown in FIG. 3d are collimating lenses (L1) and (L2) to provide collimated electromagnetic radiation to the electromagnetic beam combining means (BCM), from first (S1) and a second (S2) source of polychromatic electromagnetic radiation, ((IB1) and (IB2) respectively).

FIG. 3d further demonstrates an optional third source of polychromatic electromagnetic radiation (S3) and a second electromagnetic beam combining means (BCM'). The second electromagnetic beam combining means (BCM') is positioned with respect to said comingled beam of polychromatic electromagnetic radiation (OB), (which has a relatively broad and flattened intensity vs. wavelength over a wavelength spectrum, comprising wavelengths from sources (S1) and (S2), which exits said at least a first electromagnetic beam combining means (BCM)), such that said comingled beam of polychromatic electromagnetic radiation (OB) which has a relatively broad and flattened intensity vs. wavelength over a wavelength spectrum, passes through said second electromagnetic beam combining means (BCM). The second electromagnetic beam combining means (BCM) is positioned with respect to said third source of polychromatic electromagnetic radiation (S3) such that a beam of electromagnetic radiation from said third source of polychromatic electromagnetic radiation (S3) reflects from said second electromagnetic beam combining means (BCM) to form a second resultant beam of polychromatic electromagnetic radiation (OB') which is substantially an output beam of polychromatic electromagnetic radiation which has an even more relatively broadened and flattened intensity vs. wavelength over a wavelength spectrum comprising said comingled composite of a plurality of input beams of polychromatic electromagnetic radiation, (from sources (S1), (S2) and (S3)), which sources (S1), (S2) and (S3) individually do not provide such an even more relatively broadened and flattened intensity vs. wavelength over a wavelength spectrum characteristic. Note that first or second resultant beam of polychromatic electromagnetic radiation (OB) (OB') in FIG. 3d can be comprise the source (QTH) in FIG. 1.

A system as shown in FIG. 3d can also include a pivot(s) (PV) (PV') to allow the beam combining means (BCM) and/or (BCM'), respectively, to be rotated. This can be beneficially applied to allow selection of an optimum angle at which a beam of electromagnetic radiation is caused to reflect therefrom in use. It is noted that the angle at which a beam of electromagnetic radiation approaches a beam combining means affects the percent of an impinging beam which actually reflects therefrom and becomes part of the output beam (OB), and where a beam source positioning can be changed along with pivoting of a beam combining means, this allows optimum combining of transmitted and reflected beams. Also, pivot with two degrees of rotational freedom can be applied to simply effect coincidence of transmitted and reflected beams of electromagnetic radiation which originate from sources which are fixed in location.

Further, as described in the Disclosure of the invention Section of this Specification, as the polarizer in the present invention spectroscopic ellipsometer system remains fixed in position during data acquisition, it is preferable that a source of electromagnetic radiation, and/or a present Polarizer or Polarization State Generator be positioned or configured so as to pass predominately "S" Polarized electromagnetic radiation, as referenced to said beam combining system. The reason for this is that the split between transmission and reflection "S" polarization components is less, as a function of wavelength and electromagnetic beam angle-of-incidence to said beam combining means, compared to that between the "P" components.

It is noted that any of said sources (S1) (S2) and (S3) of polychromatic electromagnetic radiation can be Xenon or Duterium, and Quartz-Halogen lamps, or other suitable source.

It is also noted that a suitable electromagnetic beam combining (BCM) means can be made of glass or a fused silica plate, (preferably uncoated), and can also be "Hot Mirrors" which reflect IR and transmit visual wavelengths, or "Cold Mirrors" which reflect visible and transmit IR; mirror-type Beamsplitters or Pellicle Beamsplitters, such as described in Edmund Industrial Optics Catalog Number N997A.

It is also generally noted that the present invention spectroscopic ellipsometer system can, but not necessarily, utilize Zeiss Diode Array Spectrometer Systems identified by manufacturer numbers in the group: (MMS1 (300–1150 nm); UV/VIS MMS (190–730 nm); UV MMS (190–400 nm); and IR MMS (900–2400 nm)) as Detector System (DET). Said identified Zeiss systems provide a very compact system comprising a multiplicity of Detector Elements and provide focusing via a Focusing Element, Slit, and single concave holographic grating dispersive optics. However, any functional multi-element spectroscopic Detector arrangement is within the scope of the present invention.

FIGS. 4–6 are also included herein to provide insight to the Psuedo-Achromatic characteristics achieved by the FIG. 3f Compensator design. FIG. 4 shows a plot of such a compensator retardation characteristic which depends as (1/wavelength), (dashed line), as well as a present invention compensator characteristic, (solid line). The important thing to note is that a selected range of wavelengths over which a retardation of between seventy-five (75) and one-hundred-thirty (130) degrees is developed, is much greater for the present invention compensator. A present invention spectroscopic rotatable compensator ellipsometer system can comprise at least one compensator(s) which produces a retardance of, preferably, between seventy-five (75) and one-hundred-thirty (130) degrees over a range of wavelengths defined by a selection from the group consisting of:
  a. between one-hundred-ninety (190) and seven-hundred-fifty (750) nanometers;
  b. between two-hundred-forty-five (245) and nine-hundred (900) nanometers;
  c. between three-hundred-eighty (380) and seventeen-hundred (1700) nanometers;
  d. within a range of wavelengths defined by a maximum wavelength (MAXW) and a minimum wavelength (MINW) wherein the ratio of (MAXW)/(MINW) is at least one-and-eight-tenths (1.8).

Acceptable practice however, provides for the case wherein at least one of said at least one compensator(s) provides a retardation vs. wavelength characteristic retardation between thirty (30.0) and less than one-hundred-thirty-five (135) degrees over a range of wavelengths specified from MINW to MAXW by a selection from the group consisting of:
  a. MINW less than/equal to one-hundred-ninety (190) and MAXW greater than/equal to seventeen-hundred (1700);
  b. MINW less than/equal to two-hundred-twenty (220) and MAXW greater than/equal to one-thousand (1000) nanometers;
  c. within a range of wavelengths defined by a maximum wavelength (MAXW) and a minimum wavelength (MINW) range where (MAXW)/(MINW) is at least four-and one-half (4.5).

(NOTE, the specified vales and ranges can not be achieved by single plates with (1/wavelength) retardation characteristics).

More specifically, FIG. 5 shows calculated retardation vs. wavelength curves for two compensators which demonstrate (1/wavelength) retardation characteristics, (long and short dashed lines), and the retardation curve, (solid line), of a present invention assembly configuration as demonstrated in FIG. 3*f* which is arrived at by combining said two retarders with a 45 degree angle between the fast axes thereof. FIG. 6 shows a re-scaled plot of the solid line curve shown in FIG. 5.

Again, it is emphasised that the present Application does not apply Compensators in a system which causes continuous rotation thereof during data acquisition, but can benefit from a Compensator designed to provide essentially constant Polarization State Modification effects over a Spectroscopic range of wavelengths.

Continuing, the presently disclosed invention also comprises multiple element lenses which can be positioned as (FE) and/or (FE') in FIGS. 1 and 2. FIGS. 7*a*1 and 7*a*2 demonstrate the benefit possible from multiple element lenses by showing comparison Focal Length and Spot Size respectively vs. Wavelength for single and multiple element lenses. Note that the multiple element "Achromat" provides much more uniform Focal Length and Spot Size vs. Wavelength characteristics, as compared to single element Fused Silica and CaF2 lenses.

FIGS. 7*a*3 and 7*a*4 show typical single and dual multiple element lens system construction. FIG. 7*a*3 comprises three regions, two of which (FE$_{1a}$) and (FE$_{3a}$) are typically solid, while the middle region (FE$_{2a}$) can be a void, a gas, a liquid or a solid. Note that FIG. 7*a*4 has a FIG. 7*a*3 multiple element lens present and oriented rotated 180 degrees around a centrally located vertical locus. Also present is a second lens which is oriented similar to the multiple element lens of FIG. 7*a*2 and comprises elements (FE$_{1b}$) (FE$_{2b}$) and (FE$_{3b}$). Element (FE$_{2b}$) can be a void, a liquid or a solid. It is specifically noted that the use of liquid in a void between two element of a multiple element lens can provide characteristics not available where solid elements alone are present. Where gas or liquid is present between two solid elements, it should be appreciated that it can be selected to tailor desired lens characteristics in ways not possible where a solid element is present.

FIG. 7*a*5–7*a*26 show possible multiple element lens constructions. In a general sense the FIG. 7*a*5–7*a* 22 multiple element lenses are comprised of two sequentially oriented elements, one of said two sequentially oriented elements being of a shape and orientation which individually diverges a beam of electromagnetic radiation caused to pass therethrough, and the other being of a shape and orientation which individually converges a beam of electromagnetic radiation caused to pass therethrough, wherein said convergence effect is greater than said divergence effect; there being a region between said at least two elements such that, in use, a beam of electromagnetic radiation sequentially passes through one of said at least two elements, then said region therebetween, and then the other of said at least two elements before emerging as an effectively converged, focused, beam of electromagnetic radiation.

FIG. 7*a*5 shows a sequential combination of a bi-convex element and a bi-concave element.

FIG. 7*a*6 shows a sequential combination of a bi-concave element and a bi-convex element.

FIG. 7*a*7 shows a sequential combination of a bi-convex element and a plano-concave element with said concave side of said plano-concave element adjacent to said bi-convex element.

FIG. 7*a*8 shows a sequential combination of a bi-convex element and a plano-concave element with said essentially flat side of said plano-concave element being adjacent to said bi-convex element.

FIG. 7*a*9 shows a sequential combination of a plano-concave element and a bi-convex element with said essentially flat side of said plano-concave element adjacent to said bi-concave element.

FIG. 7*a*10 shows a sequential combination of a plano-concave element and bi-convex element with the concave side of said plano-concave element adjacent to said bi-convex element.

FIG. 7*a*11 shows a sequential combination of a plano-convex element and a bi-concave element with said essentially flat side of said plano-convex element adjacent to said bi-concave element.

FIG. 7*a*12 shows a sequential combination of a bi-concave element with a plano-convex element with said convex side of said plano-convex element adjacent to said bi-concave element.

FIG. 7*a*13 shows a sequential combination of a plano-concave element and a plano-convex element with the essentially flat side of said plano-concave element being adjacent to the convex side of the plano-convex element.

FIG. 7*a*14 shows a sequential combination of a plano-concave element and a plano-convex element with the essentially flat side of said planoconcave element being adjacent to the flat side of said plano-convex element.

FIG. 7*a*15 shows a sequential combination of a plano-convex element and a plano-concave element with the essentially flat side of said plano-convex element and the essentially flat side of said plano-concave element being adjacent to one another.

FIG. 7a16 shows a sequential combination of a plano-concave element and a plano-convex element with the concave side of said plano-concave element being adjacent to the convex side of the plano-convex element.

FIG. 7a17 shows a sequential combination of a plano-convex element bi-concave element with said convex side of said plano-convex element adjacent to said bi-concave element.

FIG. 7a18 shows a sequential combination of a bi-concave element and a plano-convex element with said essentially flat side of said plano-convex element adjacent to said bi-concave element.

FIG. 7a19 shows a sequential combination of a plano-convex element and a plano-concave element with said convex side of said plano-convex element adjacent to the concave side of the plano-concave element.

FIG. 7a20 shows a sequential combination of a plano-concave element and a plano-convex element with said essentially flat side of said plano-concave element being adjacent to the essentially convex side of the plano-convex element.

FIG. 7a21 shows a sequential combination of a plano-convex element and a plano-concave element with said convex side of said plano-convex element being adjacent to the essentially flat side of the plano-concave element.

FIG. 7a22 shows a sequential combination of a plano-concave element with a plano-convex element with the essentially flat side of said plano-convex element being adjacent to the concave side of said plano-concave element.

FIG. 7a23 shows that multiple element lens systems can be a sequence of at least two sequentially oriented elements characterized by being a selection from the group consisting of:
  comprising a sequential combination of a converging (C) element and a diverging (D) element;
  comprising a sequential combination of a diverging (D) element and a converging (C) element;
  comprising a sequential combination of a converging element (C), a diverging element (D), a converging element (C) and a diverging element (D);
  comprising a sequential combination of a converging element (C), a diverging (D) element, a diverging (D), element and a converging (C) element;
  comprising a sequential combination of a diverging element (D), a converging element (C), a diverging (D) element and a converging (C) element;
  comprising a sequential combination of a diverging element (D), a converging element (C), a converging element (C) and a diverging (D) element.

And, of course, other sequential lens element configurations within the scope of the present invention include:
  Converging (C), Diverging (D), Converging (C);
  Converging (C), Converging (C), Diverging (D);
  Diverging (D), Diverging (D), Converging (C);
  Converging (C), Diverging (D), Diverging (D);
  Diverging (D), Converging (C), Diverging (D);
  Diverging (D), Converging (C), Converging (C);
  Converging (C), Converging (C), Diverging (D), Diverging (D); and
  Diverging (D), Diverging (D), Converging (C), Converging (C).

FIGS. 7a27–7a32 show three element lens constructions.

It is noted that multiple element lenses can include a converging element selected from the group consisting of:
  a positive miniscus;
  an asymmetric convex;

and/or a diverging element selected from the group consisting of:
  a negative miniscus;
  an asymmetric concave;

where miniscus refers to a bi-concave element wherein the radius of curvature is different for the two concave aspects thereof.

It is specifically noted that while the lenses shown in FIGS. 7a3, 7a4 and 7a5–7a26 are typically selected to demonstrate radial symmetry, it is within the scope of the present invention to utilize non-radially symmetric lenses, where, for instance, a spot size length to width aspect ratio is to be modified thereby. Therefore any lens shown or indicated in FIGS. 7a3, 7a4 and 7a5–7a26 can be designed to demonstrate radial symmetry, or non-radial symmetry, or be of any other functional type, where the achromatic properties are present.

FIG. 8 is included to disclose to show that the presently disclosed spectroscopic ellipsometer can be contained within a Chamber (CHA) System for controlling the ambient atmosphere. Possible Chamber configurations are:
  it comprises at least one chamber region in which is present polarization state generator (PSG) comprising component(s) prior to said material system (SS), said material system (SS), and polarization state detector (PSD) comprising component(s) after said material system (SS);
  it comprises at least three chamber regions, in one of which is present polarization state generator (PSG) comprising component(s) prior to said material system (SS), in the second of which is present the material system (SS) and in the third of which is present polarization state detector (PSD) comprising component(s) after said material system (SS);
  it comprises at least two chamber regions, in one of which is present polarization state generator (PSG) comprising component(s) prior to said material system (SS) and said material system (SS), and in the second of which is present polarization state detector (PSD) comprising component(s) after said material system (SS);
  it comprises at least two chamber regions, in one of which is present polarization state generator (PSD) comprising component(s) prior to said material system (SS), and in the second of which is present polarization state detector (PSD) comprising component(s) after said material system (SS) and said material system (SS);

where the combination of elements (QTH), (P), and (DSP') in FIG. 1 is described as a Polarization State Generation System (PSG), and the combination of elements (DSP) (A) and (DET) is described as a Polarization State Detection System (PSD).

It is noted that the terminology Polarizer (P), Analyzer (A), Compensator (C) include any element which performs the described function.

Finally, it is to be understood that the terminology "spectroscopic ellipsometer system is to be read with sufficient breadth to include spectroscopic polarimeter and the like systems.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for monitoring change in:
   the intensity of; and/or
   the ratio of and/or
   the phase between orthogonal components in;
   a spectroscopic beam of electromagnetic radiation which is caused by interaction with a material system;
   said system comprising at least one lens which is of multiple element construction and positioned so that beam of electromagnetic radiation transmits therethrough, wherein, at least two elements thereof are made from different materials, such that in use the focal length for each wavelength in a range of wavelengths is within an acceptable range of focal lengths;
   said at least one multiple element lens being characterized by at least one selection from the group consisting of:
   a) the focal length is between forty and forty-one millimeters over a range of wavelengths of at least two-hundred to seven-hundred nanometers;
   b) the focal length varies by less than five (5%) percent over a range of wavelengths of between two-hundred and five-hundred nanometers; and
   c) the spot diameter at the focal length is less than seventy-five microns over a range of wavelengths of at least two-hundred to seven-hundred nanometers;
   said system further comprising at least one compensator positioned so that beam of electromagnetic radiation transmits therethrough, said compensator being characterized by a selection from the group consisting of:
   said at least one compensator produces a retardence of between seventy-five (75) and one-hundred-thirty (130) degrees over a range of wavelengths defined by a selection from the group consisting of:
   a) between one-hundred-ninety (190) and seven-hundred-fifty (750) nanometers;
   b) between two-hundred-forty-five (245) and nine-hundred (900) nanometers;
   c) between three-hundred-eighty (380) and seventeen-hundred (1700) nanometers;
   d) within a range of wavelengths defined by a maximum wavelength (MAXW) and a minimum wavelength (MINW) wherein the ratio of (MAXW)/(MINW) is at least one-and-eight-tenths (1.8); and
   said at least one compensator produces a retardation between thirty (30.0) and less than one-hundred-thirty-five (135) degrees over a range of wavelengths specified from MINW to MAXW by a selection from the group consisting of:
   a) MINW less than/equal to one-hundred-ninety (190) and MAXW greater than/equal to seventeen-hundred (1700);
   b) MINW less than/equal to two-hundred-twenty (220) and MAXW greater than/equal to one-thousand (1000) nanometers;
   c) within a range of wavelengths defined by a maximum wavelength (MAXW) and a minimum wavelength (MINW) range where (MAXW)/(MINW) is at least four-and one-half (4.5).

2. A system as in claim 1, in which said at least one multiple element lens demonstrates birefringence.

3. A system as in claim 1, in which said at least one multiple element lens comprises at least two elements which are made from different materials independently selected from the group consisting of:
   $CaF_2$;
   $BaF_2$;
   LiF;
   $MgF_2$;
   fused silica;
   a void region;
   a gas filled region;
   a liquid filled region; and
   a functional equivalent to a void region.

4. A system as in claim 1 in which, during data collection, said at least one compensator is caused to perform motion selected from the group consisting of:
   continuously rotates; and
   sequentially rotates through a plurality of discrete angles;
   around an axis defined by the locus of the spectroscopic electromagnetic beam as it transmits therethrough.

5. A system as in claim 1 which is present in a Chamber configured as a selection from the group consisting of:
   it comprises at least one chamber region in which is present polarization state generator comprising component(s) prior to said material system, said material system, and polarization state detector comprising component(s) after said material system;
   it comprises at least three chamber regions, in one of which is present polarization state generator comprising component(s) prior to said material system, in the second of which is present the material system and in the third of which is present polarization state detector comprising component(s) after said material system;
   it comprises at least two chamber regions, in one of which is present polarization state generator comprising component(s) prior to said material system and said material system, and in the second of which is present polarization state detector comprising component(s) after said material system;
   it comprises at least two chamber regions, in one of which is present polarization state generator comprising component(s) prior to said material system, and in the second of which is present polarization state detector comprising component(s) after said material system and said material system.

* * * * *